United States Patent
Boyd et al.

(10) Patent No.: US 11,180,477 B2
(45) Date of Patent: Nov. 23, 2021

(54) PROCESS FOR THE PREPARATION OF OSIMERTINIB (AZD9291) OR A SALT THEREOF, AND "AZD9291 ANILINE" OR A SALT THEREOF

(71) Applicant: AstraZeneca AB, Södertälje (SE)

(72) Inventors: Alistair John Boyd, Macclesfield (GB); Alexander Telford, Macclesfield (GB)

(73) Assignee: AstraZeneca AB, Sodertalje (SE)

( * ) Notice: Subject to any disclaimer, the term of this patent is extended or adjusted under 35 U.S.C. 154(b) by 586 days.

(21) Appl. No.: 16/074,119

(22) PCT Filed: Jan. 31, 2017

(86) PCT No.: PCT/EP2017/052050
§ 371 (c)(1),
(2) Date: Jul. 31, 2018

(87) PCT Pub. No.: WO2017/134051
PCT Pub. Date: Aug. 10, 2017

(65) Prior Publication Data
US 2021/0122734 A1    Apr. 29, 2021

Related U.S. Application Data

(60) Provisional application No. 62/289,390, filed on Feb. 1, 2016.

(51) Int. Cl.
C07D 401/04 (2006.01)
C07D 403/04 (2006.01)

(52) U.S. Cl.
CPC ................. *C07D 403/04* (2013.01)

(58) Field of Classification Search
CPC .................................................. C07D 401/04
See application file for complete search history.

(56) References Cited

U.S. PATENT DOCUMENTS 4,070,401 A    1/1978    Hirai et al.

FOREIGN PATENT DOCUMENTS

| CN | 104817541 A | 8/2015 |
|---|---|---|
| WO | 2013014448 A1 | 1/2013 |
| WO | 2015195228 A1 | 12/2015 |

OTHER PUBLICATIONS

Berge et al., Journal of Pharmaceutical Sciences, 1977.
Ward et al.; "Structure-and Reactivity-Based Development of Covalent Inhibitors of the Activating and Gatekeeper Mutant Forms of the Epidermal Growth Factor Receptor (EGFR)," Journal of Medicinal Chemistry, 2013, 56, pp. 7025-7048.

*Primary Examiner* — Patricia L Morris

(57) ABSTRACT

An improved chemical process for the manufacture of the compound of Formula (I), which is useful, for example, as a late-stage chemical intermediate in the production of osimertinib (AZD9291) and pharmaceutically acceptable salts thereof.

19 Claims, No Drawings

PROCESS FOR THE PREPARATION OF OSIMERTINIB (AZD9291) OR A SALT THEREOF, AND "AZD9291 ANILINE" OR A SALT THEREOF

CROSS-REFERENCE TO RELATED APPLICATIONS

This application is a U.S. National Stage application of International Application No. PCT/EP2017/052050, filed on Jan. 31, 2017, said International Application No. PCT/EP2017/052050 claims benefit under 35 U.S.C. § 119(e) of U.S. Provisional Application No. 62/289,390, filed Feb. 1, 2016. Each of the above listed applications is incorporated by reference herein in its entirety for all purposes.

Osimertinib (also known as "AZD9291") is a compound in clinical development for certain types of cancer, in particular, certain types of non-small cell lung cancer (NSCLC). It may be used in the form of a free base, or as a pharmaceutically acceptable salt, such as, for example, a mesylate salt. The present disclosure relates to an improved chemical process for the preparation of the compound of Formula (I), or a salt thereof.

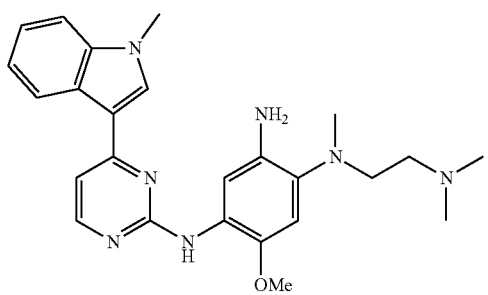

(I)

The compound of Formula (I), or a salt thereof, is useful as a late-stage intermediate in the preparation of osimertinib, and in the preparation of pharmaceutically acceptable salts of osimertinib. The compound of Formula (I) is referred to herein as "AZD9291 Aniline" and may also be known by the chemical name: $N^1$-(2-dimethylaminoethyl)-5-methoxy-N-methyl-$N^4$-[4-(1-methylindol-3-yl)pyrimidin-2-yl]benzene-1,2,4-triamine.

The chemical structure of osimertinib (also known as "AZD9291") is shown below as Formula (II):

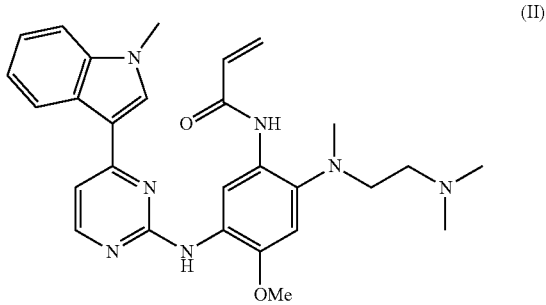 [SMILES: C=CC(=O)Nc1cc(Nc2nccc(-c3cn(C)c4ccccc34)n2)c(OC)cc1N(C)CCN(C)C]

(II)

International Patent Publication No. WO2013/014448 discloses AZD9291 and pharmaceutically acceptable salts of AZD9291. It also discloses that AZD9291 may be obtained by reaction of AZD9291 Aniline with an activated acrylic acid derivative or precursor, (for example acryloyl chloride), preferably in the presence of a suitable base, (for example a trialkylamine base) as shown in Scheme 1 below:

Scheme 1

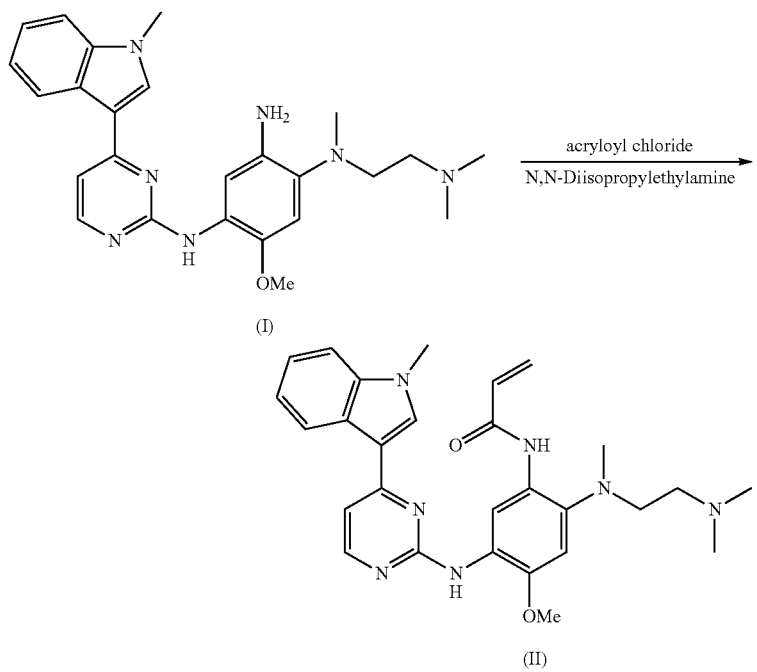

WO2013/014448 also discloses that AZD9291 may be obtained from AZD9291 Aniline by reaction with 3-chloropropanoyl chloride. In one example sodium hydroxide is used as a base. In another example, potassium carbonate and triethylamine are used as bases in order to provide AZD9291 as shown in Scheme 2 below:

Scheme 2

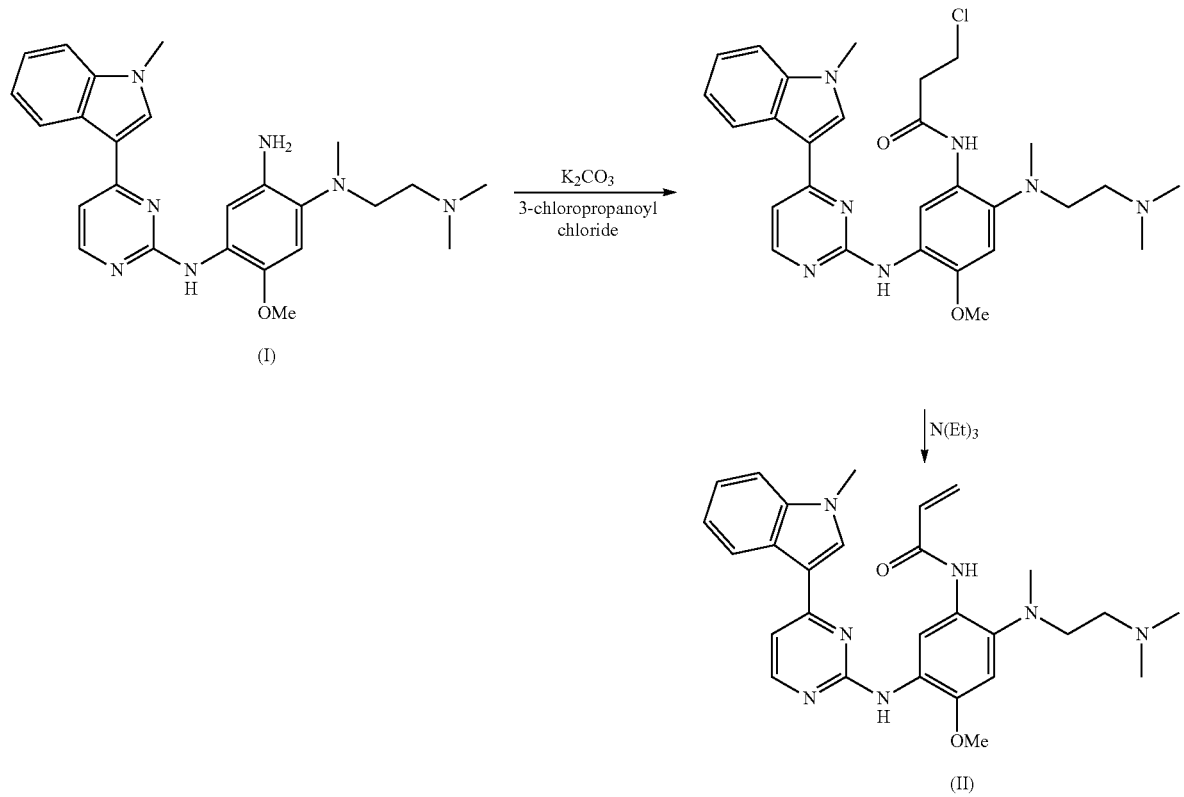

WO2013/014448 also describes a process for the preparation of AZD9291 Aniline from the compound of Formula (III), as shown in Scheme 3 below.

Scheme 3

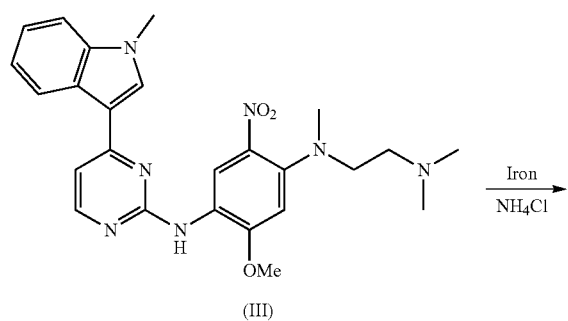

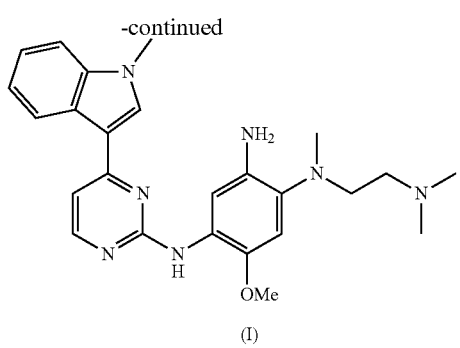

-continued

The compound of Formula (III) is referred to herein as "AZD9291 Nitrodiamine" and may be known by the chemical name: $N^1$-[2-(dimethylamino)ethyl]-5-methoxy-N-methyl-$N^4$-[4-(1-methylindol-3-yl)pyrimidin-2-yl]-2-nitrobenzene-1,4-diamine.

The process described in WO2013/014448 (shown in Scheme 3 above) uses iron as a reducing agent. The skilled person will appreciate that iron-based residues, such as iron oxide, would be present in the reaction mixture, and that such residues may be practically troublesome to remove, especially on large scale, for example, as part of any manufacture of AZD9291 (or a pharmaceutically acceptable salt thereof). Extra processing steps may be required to remove the significant quantities of iron residues during a commercial-scale manufacture.

Alternatively, we have now found that AZD9291 Aniline may be prepared by the reduction of AZD9291 Nitrodiamine by hydrogenation of AZD9291 Nitrodiamine in the presence of a palladium-on-carbon catalyst or platinum-on-carbon catalyst. However, having selected a platinum-on-carbon catalyst, we were surprised to find that a troublesome impurity could form during the hydrogenation of AZD9291 Nitrodiamine to AZD9291 Aniline. We have identified the structure of the troublesome impurity and its chemical structure is shown as Formula (IV) below:

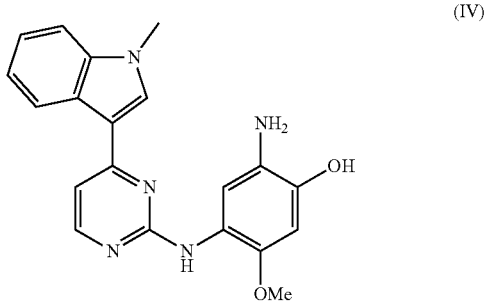 [SMILES: COc1cc(O)c(N)cc1Nc1nccc(-c2cn(C)c3ccccc23)n1]

(IV)

The compound of Formula (IV) is referred to herein as "AZD9291 Aniline Hydroxy" and may also be known by the chemical name: [2-amino-5-methoxy-4-(4-(1-methylindol-3-yl)pyrimidin-2-ylamino)phenol]. We also found that AZD9291 Aniline Hydroxy can lead to the formation of further degradation products during the synthesis of AZD9291 Aniline. Collectively, these unwanted impurities can be troublesome to remove and one or more of them are darkly coloured. Thorough process chemistry investigations have ultimately uncovered conditions that allow for removal of impurities during our downstream processing, but clearly it would be preferable to avoid/minimise the initial formation of such impurities, if at all possible.

It will be appreciated that impurity levels in a pharmaceutical product and late-stage pharmaceutical intermediates need to be controlled to a suitably safe level. For all pharmaceutical products, it is important to establish a manufacturing process which is robust and refined enough to reliably deliver material of a predefined high quality. At the same time, the process needs to be suitable for large scale manufacture in order to provide enough AZD9291 (or pharmaceutically acceptable salt thereof) to meet worldwide demand.

We have surprisingly discovered an improved process for the preparation of AZD9291 Aniline (or salt thereof). The improved process results in an improved impurity profile of AZD9291 Aniline, where the impurity AZD9291 Aniline Hydroxy does not appear to be formed at all, according to our assays. In turn, the absence of AZD9291 Aniline Hydroxy reduces the potential for formation of further degradation products. AZD9291 Aniline prepared by the improved process may be further processed to provide AZD9291 or a pharmaceutically acceptable salt of AZD9291, for example AZD9291 mesylate. This improved process has the potential to reduce the risk of the batch failure, increase the yield of the reaction, and to increase the overall yield of AZD9291 (or pharmaceutically acceptable salt thereof) as a consequence. This may provide a cost and/or time benefit as fewer batches of material may need to be reprocessed or abandoned.

Accordingly there is provided an improved process for the preparation of AZD9291 or a pharmaceutically acceptable salt thereof, which comprises:
a) reaction of AZD9291 Nitrodiamine of Formula (III), or a salt thereof

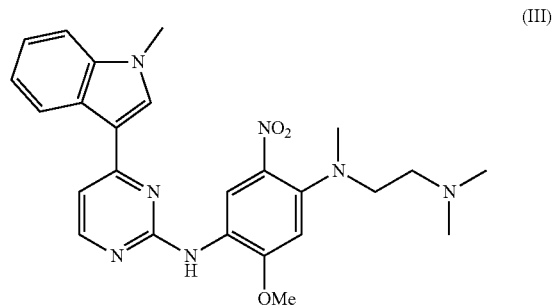 [SMILES: COc1cc(N(C)CCN(C)C)c([N+](=O)[O-])cc1Nc1nccc(-c2cn(C)c3ccccc23)n1]

(III)

with hydrogen, in the presence of a palladium(0)- and/or platinum(0)-based catalyst, and in the presence of an acid, to form AZD9291 Aniline of Formula (I), or a salt thereof

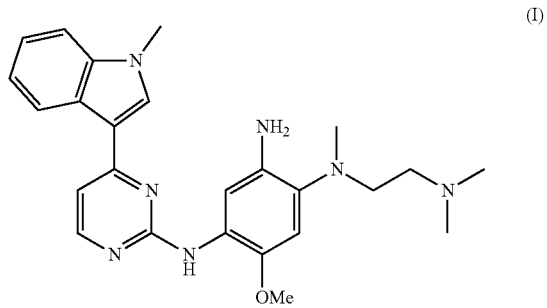 [SMILES: COc1cc(N(C)CCN(C)C)c(N)cc1Nc1nccc(-c2cn(C)c3ccccc23)n1]

(I)

wherein the reaction is carried out in the presence of water, or in the presence of a mixture of water and a water-miscible solvent;
b) reaction of the resulting AZD9291 Aniline or salt thereof with an activated acrylic acid derivative or precursor, and where necessary, treatment with base to form AZD9291 of Formula (II):

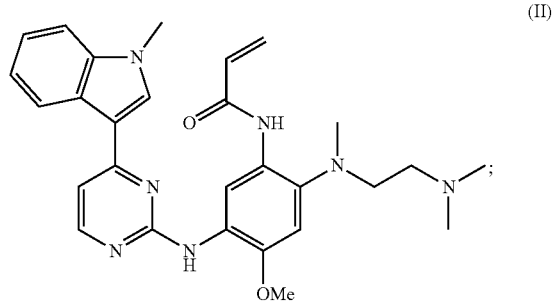 [SMILES: C=CC(=O)Nc1cc(Nc2nccc(-c3cn(C)c4ccccc34)n2)c(OC)cc1N(C)CCN(C)C]

(II)

c) optional formation of a pharmaceutically acceptable salt thereof.

In one embodiment, the pharmaceutically acceptable salt of AZD9291 is a mesylate salt.

It may be appreciated by a person skilled in the art that the addition of acid to the process to manufacture AZD9291 Aniline, in the presence of water (or in the presence of a mixture of water and a water-miscible solvent) would be expected to favour the formation of an impurity such as AZD9291 Aniline Hydroxy, due to the presence of water (which could act as a reactant) and presence of acid (which could act as catalyst for hydrolysis). However, surprisingly, against such expectations, we have found that the addition of acid to the process to manufacture AZD9291 Aniline actually results in significantly lower levels of the hydrolysis product, (AZD9291 Aniline Hydroxy) being generated. In fact, in the examples described hereinafter, AZD9291 Aniline Hydroxy is non-detectable using our standard analytical methods.

Therefore, it will be appreciated that the process of the present disclosure results in significant manufacturing advantages, for example: (1) a lower risk of batch failures due to an improved impurity profile; (2) simpler downstream processing to deliver AZD9291 (or pharmaceutically acceptable salt thereof) of sufficient purity for pharmaceutical use; (3) the potential to increase the yield of the reaction to prepare AZD9291 Aniline and consequently AZD9291; and (4) an opportunity to simplify the process to prepare AZD9291 Aniline itself.

Step a)

It will be appreciated that the palladium(0)-based catalysts and the platinum(0)-based catalysts may be provided on activated carbon. It is to be understood that the amount of catalyst present in the reaction mixture is generally quoted herein as the molar amount of platinum and/or palladium metal present in the catalyst(s) rather than the total weight of catalyst present (which could, for example, include moisture, and any support—such as activated carbon, etc), and the amount of catalyst, when "molar equivalents" are mentioned, is relative to the amount of AZD9291 Nitrodiamine used in the reaction. Therefore, quoting the amount of catalyst present as the amount of platinum and/or palladium takes into account variations in precious metal content of the catalyst, which can vary due to reasons such as the precious metal loading, the amount of activated carbon support and the water content of the catalyst.

Suitably, the catalyst is a palladium(0)- and/or platinum(0)-based catalyst.

In one embodiment the palladium(0)- and/or platinum(0)-based catalyst contains at least 0.0005 molar equivalents of palladium(0).

In one embodiment the palladium(0)- and/or platinum(0)-based catalyst contains at least 0.001 molar equivalents of palladium(0).

In one embodiment the palladium(0)- and/or platinum(0)-based catalyst contains at least 0.005 molar equivalents of palladium(0).

In one embodiment the palladium(0)- and/or platinum(0)-based catalyst contains at least 0.0001 molar equivalents of platinum(0).

In one embodiment the palladium(0)- and/or platinum(0)-based catalyst contains at least 0.0002 molar equivalents of platinum(0).

In one embodiment the palladium(0)- and/or platinum(0)-based catalyst contains at least 0.001 molar equivalents of platinum(0).

In one embodiment, the palladium(0)- and/or platinum(0)-based catalyst is on activated carbon.

In one embodiment the palladium(0)- and/or platinum(0)-based catalyst comprises a palladium(0)-based catalyst.

In one embodiment, the palladium(0)-based catalyst contains one or more additional metals in addition to the palladium(0).

In a further embodiment, the metal in the palladium(0)-based catalyst is predominately palladium(0).

In one embodiment the palladium(0)- and/or platinum(0)-based catalyst is a palladium(0)-based catalyst.

In one embodiment, the palladium(0)-based catalyst contains at least 0.0005 molar equivalents of palladium(0).

In another embodiment, the palladium(0)-based catalyst contains at least 0.001 molar equivalents of palladium(0).

In another embodiment, the palladium(0)-based catalyst contains at least 0.005 molar equivalents of palladium(0).

In a further embodiment, the palladium(0)-based catalyst contains 0.005 molar equivalents of palladium(0).

In one embodiment the palladium(0)- and/or platinum(0)-based catalyst comprises a platinum(0)-based catalyst.

In another embodiment, the platinum(0)-based catalyst contains one or more additional metals in addition to the platinum(0).

In another embodiment, the metal in the platinum(0)-based catalyst is predominately platinum(0).

In one embodiment, the palladium(0)- and/or platinum(0)-based catalyst is a platinum(0)-based catalyst.

In one embodiment, the platinum(0)-based catalyst contains at least 0.0001 molar equivalents of platinum(0).

In another embodiment, the platinum(0)-based catalyst contains at least 0.0002 molar equivalents of platinum(0).

In another embodiment, the platinum(0)-based catalyst contains at least 0.001 molar equivalents of platinum(0).

In a further embodiment, the platinum(0)-based catalyst contains 0.001 molar equivalents of platinum(0).

In one aspect, one or more additional transition metals may be present in the catalyst together with the platinum and/or palladium, such as vanadium, for example a mixture of platinum and vanadium in at least 1:1 mass ratio, for example 1:2. In this aspect, the platinum(0) or palladium(0) present in the catalyst is believed to be the metal which is predominantly responsible for catalysing the reaction.

In one embodiment:

the palladium(0)-based catalyst on activated carbon contains at least 0.0001 molar equivalents of palladium(0);

the platinum(0)-based catalyst on activated carbon contains at least 0.0005 molar equivalents of platinum(0); or the (platinum(0) and vanadium)-based catalyst on activated carbon, wherein the mass ratio of platinum(0) to vanadium in the catalyst is 1:2, contains at least 0.0005 molar equivalents of platinum(0).

Suitably, the reaction of AZD9291 Nitrodiamine (or a salt thereof) to form AZD9291 Aniline (or a salt thereof) is carried out in the presence of an acid.

Suitable acids are Bronsted acids, for example, carboxylic acids, sulfonic acids and mineral acids which are miscible with and/or soluble in water or a mixture of water and a water-miscible solvent.

In one embodiment, the acid is a Bronsted acid.

In one embodiment, the acid is a Bronsted acid that is miscible with and/or soluble in water or a mixture of water and a water-miscible solvent.

In one embodiment, the acid comprises an acid selected from a carboxylic acid, a sulfonic acid and a mineral acid.

In one embodiment, the acid comprises an acid selected from a carboxylic acid, a sulfonic acid and a mineral acid that is miscible with and/or soluble in water or a mixture of water and a water-miscible solvent.

In one embodiment, the acid comprises a carboxylic acid.

In one embodiment, the acid comprises a carboxylic acid that is miscible with and/or soluble in water or a mixture of water and a water-miscible solvent.

In one embodiment, the acid comprises a sulfonic acid.

In one embodiment, the acid comprises a sulfonic acid that is miscible with and/or soluble in water or a mixture of water and a water-miscible solvent.

In another embodiment, the acid comprises a mineral acid.

In another embodiment, the acid comprises a mineral acid that is miscible with and/or soluble in water or a mixture of water and a water-miscible solvent.

In one embodiment, the carboxylic acid comprises an acid selected from ($C_{1-7}$hydrocarbyl)COOH, formic acid, trichloroacetic acid and trifluoroacetic acid. An example of a ($C_3$hydrocarbyl)-COOH is n-butanoic acid. An example of a ($C_6$hydrocarbyl)COOH is benzoic acid.

In another embodiment, the carboxylic acid comprises an acid selected from acetic acid and trifluoroacetic acid.

In another embodiment, the sulfonic acid comprises an acid selected from methanesulfonic acid, benzenesulfonic acid and p-toluenesulfonic acid.

In another embodiment, the sulfonic acid comprises an acid selected from methanesulfonic acid and benzenesulfonic acid.

In another embodiment, the mineral acid comprises an acid selected from hydrochloric acid, sulfuric acid and phosphoric acid.

In another embodiment, the acid comprises an acid selected from ($C_{1-7}$hydrocarbyl)COOH, formic acid, trichloroacetic acid, trifluoroacetic acid, methanesulfonic acid, benzenesulfonic acid, p-toluenesulfonic acid, hydrochloric acid, sulfuric acid and phosphoric acid.

In another embodiment, the acid comprises an acid selected from acetic acid, trifluoroacetic acid, methanesulfonic acid, benzenesulfonic acid, hydrochloric acid, sulfuric acid and phosphoric acid.

In one embodiment, the acid comprises ($C_{1-7}$hydrocarbyl)COOH.

In one embodiment, the acid comprises acetic acid.

In one embodiment, the acid comprises formic acid.

In one embodiment, the acid comprises trichloroacetic acid.

In one embodiment, the acid comprises trifluoroacetic acid.

In one embodiment, the acid comprises methanesulfonic acid.

In one embodiment, the acid comprises benzenesulfonic acid.

In one embodiment, the acid comprises p-toluenesulfonic acid.

In one embodiment, the acid comprises hydrochloric acid.

In one embodiment, the acid comprises sulfuric acid.

In one embodiment, the acid comprises phosphoric acid.

In one embodiment, the acid is ($C_7$hydrocarbyl)COOH.

In one embodiment, the acid is acetic acid.

In one embodiment, the acid is formic acid.

In one embodiment, the acid is trichloroacetic acid.

In one embodiment, the acid is trifluoroacetic acid.

In one embodiment, the acid is methanesulfonic acid.

In one embodiment, the acid is benzenesulfonic acid.

In one embodiment, the acid is p-toluenesulfonic acid.

In one embodiment, the acid is hydrochloric acid.

In one embodiment, the acid is sulfuric acid.

In one embodiment, the acid is phosphoric acid.

In a further aspect, at least 1.0 molar equivalents of acid is used. In one embodiment, 1.0-2.0 molar equivalents of acid is used. In another embodiment, 1.4-1.6 molar equivalents of acid is used. In a further embodiment, 1.6 molar equivalents of acid is used. Conveniently 1.5 molar equivalents of acid is used. It is to be understood that the amount (molar equivalents) of acid added is relative to the amount of AZD9291 Nitrodiamine.

Suitably, the reaction of AZD9291 Nitrodiamine (or salt thereof) to form AZD9291 Aniline (or salt thereof) is carried out in the presence of water, or in the presence of a mixture of water and a water-miscible solvent. When it is stated that "the reaction is carried out in the presence of water, or in the presence of a mixture of water and a water-miscible solvent" it is to be understood that some, all or none of said water could originate from the acid that is used in the reaction (if the acid that is used contains some water—for example, hydrochloric acid).

In one embodiment, the reaction is carried out in the presence of water.

In one embodiment, the reaction is carried out in water.

In another embodiment, the reaction is carried out in the presence of a mixture of water and a water-miscible solvent.

In further embodiments, the water-miscible solvent is selected from an alcohol, tetrahydrofuran, acetonitrile, dimethyl sulfoxide, dimethylformamide, dimethylacetamide and N-methylpyrrolidin-2-one.

In an embodiment, the water-miscible solvent is selected from an alcohol, tetrahydrofuran, acetonitrile, dimethyl sulfoxide and N-methylpyrrolidin-2-one.

In another embodiment, the water-miscible solvent is selected from ($C_{1-6}$alkyl)-OH, tetrahydrofuran, acetonitrile, dimethyl sulfoxide, dimethylformamide, dimethylacetamide and N-methylpyrrolidin-2-one.

An example of a ($C_3$alkyl)-OH is isopropanol. An example of a ($C_5$alkyl)-OH is cyclopentanol.

In a further embodiment, the water-miscible solvent is selected from methanol, ethanol, propanol, tetrahydrofuran, acetonitrile, dimethyl sulfoxide, dimethylformamide, dimethylacetamide and N-methylpyrrolidin-2-one. In another embodiment, the water-miscible solvent is selected from methanol, ethanol, n-propanol, isopropanol, tetrahydrofuran, acetonitrile, dimethyl sulfoxide dimethylformamide, dimethylacetamide and N-methylpyrrolidin-2-one. In a further embodiment, the water-miscible solvent is selected from methanol, iso-propanol, tetrahydrofuran, acetonitrile, dimethyl sulfoxide and N-methylpyrrolidin-2-one.

In one embodiment, the water-miscible solvent comprises ($C_{1-6}$alkyl)-OH.

In one embodiment, the water-miscible solvent comprises methanol.

In one embodiment, the water-miscible solvent comprises ethanol.

In one embodiment, the water-miscible solvent comprises propanol.

In one embodiment, the water-miscible solvent comprises n-propanol.

In one embodiment, the water-miscible solvent comprises isopropanol.

In one embodiment, the water-miscible solvent comprises tetrahydrofuran.

In one embodiment, the water-miscible solvent comprises acetonitrile.

In one embodiment, the water-miscible solvent comprises dimethyl sulfoxide.

In one embodiment, the water-miscible solvent comprises dimethylformamide.

In one embodiment, the water-miscible solvent comprises dimethylacetamide.

In one embodiment, the water-miscible solvent comprises N-methylpyrrolidin-2-one.

In one embodiment, the water-miscible solvent is ($C_{1-6}$alkyl)-OH.

In one embodiment, the water-miscible solvent is methanol.

In one embodiment, the water-miscible solvent is ethanol.

In one embodiment, the water-miscible solvent is propanol.

In one embodiment, the water-miscible solvent is n-propanol.

In one embodiment, the water-miscible solvent is isopropanol.

In one embodiment, the water-miscible solvent is tetrahydrofuran.

In one embodiment, the water-miscible solvent is acetonitrile.

In one embodiment, the water-miscible solvent is dimethyl sulfoxide.

In one embodiment, the water-miscible solvent is dimethylformamide.

In one embodiment, the water-miscible solvent is dimethylacetamide.

In one embodiment, the water-miscible solvent is N-methylpyrrolidin-2-one.

Further suitable conditions are as described in the examples herein.

It will be understood that a mixture of water and a water-miscible solvent will be construed to mean the mixture may contain more than one water-miscible solvent.

In one embodiment, the mixture of water and a water-miscible solvent is as defined herein, with the proviso that water-miscible solvent does not comprise a ketone solvent, such as acetone.

The reactions with hydrogen as described herein is preferably carried out at a pressure of >0.2 bar, for example 0.2-10 bar. Accordingly in one embodiment the reaction with hydrogen is carried out at a pressure of more than 0.2 bar. In a further embodiment the reaction with hydrogen is carried out at a pressure in the range from 0.2 to 10 bar. In a further embodiment the reaction with hydrogen is carried out at a pressure of 2.5 to 3.5 bar, such as 3 bar.

The reactions with hydrogen as described herein is preferably carried out at a pressure of >0.2 barg, for example 0.2-10 barg. Accordingly in one embodiment the reaction with hydrogen is carried out at a pressure of more than 0.2 barg. In a further embodiment the reaction with hydrogen is carried out at a pressure in the range from 0.2 to 10 barg. In a further embodiment the reaction with hydrogen is carried out at a pressure of 1.5 to 2.5 barg, such as 2 barg.

The reactions with hydrogen as described herein is preferably carried out at a temperature of >0° C., for example 0-70° C. Accordingly in one embodiment the reaction with hydrogen is carried out at a temperature of more than 0° C. In a further embodiment the reaction with hydrogen is carried out at a temperature in the range from 0 to 70° C. In a further embodiment the reaction with hydrogen is carried out at a temperature in the range from 40 to 60° C., such as 45 to 55° C., such as 50° C.

Step b)

Particular examples of suitable "activated acrylic acid derivatives or precursors" are acryloyl halide or 3-halopropanoyl analogues, wherein halide is chloride or bromide, and wherein halo is chloro or bromo. Alternative activated acrylic acid derivatives or precursors, which could deliver the required acryloyl functionality, are known in the art. Such alternatives could include, for example, variants of acryloyl halide or 3-halopropanoyl halide wherein an alternative leaving group is used in place of the halide. Other methodologies may use, for example, acrylic acid but employ conditions where acryloyl halide is formed in-situ in the reaction mixture. Similarly, 3-chloropropanoic acid or acrylic acid may be used together with an amide coupling agent. Methodologies for coupling carboxylic acids to amino groups are well-known in the art.

Therefore, in one embodiment the activated acrylic acid derivative or precursor is selected from acryloyl halide and 3-halopropanoyl halide (wherein the halide and halo are each independently selected from chloro and bromo); or is selected from 3-chloropropanoic acid and acrylic acid, where amide coupling conditions are used.

Accordingly, in one embodiment the activated acrylic acid derivative or precursor is selected from acryloyl halide and 3-halopropanoyl halide (wherein the halide and halo are each independently selected from chloro and bromo); or is selected from 3-chloropropanoic acid and acrylic acid, where an amide coupling agent is used.

Therefore, in one embodiment the activated acrylic acid derivative or precursor is selected from acryloyl halide and 3-halopropanoyl halide, wherein the halide and halo are each independently selected from chloro and bromo.

In one embodiment, the activated acrylic acid derivative or precursor is acryloyl chloride or 3-chloropropanoyl chloride.

In one embodiment, the activated acrylic acid derivative or precursor is acryloyl chloride.

In another embodiment, the activated acrylic acid derivative or precursor is 3-chloropropanoyl chloride.

In one aspect, there is provided the reaction of the resulting AZD9291 Aniline (or salt thereof) with an activated acrylic acid derivative or precursor, and where necessary, treatment with base to form AZD9291 (or a pharmaceutically acceptable salt thereof). In one embodiment, there is provided reaction of the resulting AZD9291 Aniline (or salt thereof) with an activated acrylic acid derivative or precursor, and treatment with base to form AZD9291 (or a pharmaceutically acceptable salt thereof). In one aspect, there is provided the reaction of the resulting AZD9291 Aniline (or salt thereof) with an acryloyl halide or 3-halopropanoyl analogues (wherein halide is chloride or bromide, and wherein halo is chloro or bromo) and where necessary, treatment with base to form AZD9291 (or a pharmaceutically acceptable salt thereof). In one embodiment, there is provided reaction of the resulting AZD9291 Aniline (or salt thereof) with an acryloyl halide or 3-halopropanoyl halide, (wherein halide is chloride or bromide, and wherein halo is chloro or bromo) and treatment with base to form AZD9291 (or a pharmaceutically acceptable salt thereof). In a further embodiment, there is provided reaction of the resulting AZD9291 Aniline (or salt thereof) with acryloyl chloride or 3-chloropropanoyl chloride, and treatment with base to form AZD9291 (or a pharmaceutically acceptable salt thereof). In another embodiment, there is provided reaction of the resulting AZD9291 Aniline (or salt thereof) with an activated acrylic acid derivate or precursor. In one embodiment, there is provided reaction of the resulting AZD9291 Aniline (or salt thereof) with an acryloyl halide or 3-halopropanoyl halide, (wherein halide is chloride or bromide, and wherein halo is chloro or bromo). In a further embodiment, there is provided reaction of the resulting AZD9291 Aniline (or salt thereof) with acryloyl chloride or 3-chloropropanoyl chloride. It will be appreciated by a person skilled in the art that depending on the type of activated acrylic acid derivative or precursor used, that the treatment by base to form AZD9291 may or may not be necessary. It will be appreciated by a person skilled in the art if treatment by base is required, that the base may be added to reaction mixture at the same time as the other reactants, for example at the same time as AZD9291 Aniline (or a salt thereof) and an activated acrylic acid derivative or precursor, or at a different point in the reaction sequence.

Step c)

Suitable pharmaceutically acceptable salts are an acid addition salts, such as an acid addition salt formed using an inorganic acid or organic acid. In one embodiment, an acid addition salt may be formed using an inorganic acid selected from hydrochloric acid, hydrobromic acid, sulphuric acid and phosphoric acid. In another embodiment, an acid addition salt may be formed using an organic acid selected from trifluoroacetic acid, citric acid, maleic acid, oxalic acid, acetic acid, formic acid, benzoic acid, fumaric acid, succinic acid, tartaric acid, lactic acid, pyruvic acid, methanesulfonic acid, benzenesulfonic acid and p-toluenesulfonic acid. In one embodiment, a pharmaceutical acceptable salt is a mesylate salt.

In a further aspect of the present disclosure, there is provided an improved process for the manufacture of AZD9291 or a pharmaceutically acceptable salt thereof which comprises:
  a) reaction of AZD9291 Nitrodiamine or a salt thereof with hydrogen, in the presence of a palladium(0)- and/or platinum(0)-based catalyst, and in the presence of an acid wherein the acid comprises an acid selected from a carboxylic acid, a sulfonic acid and a mineral acid, to form AZD9291 Aniline or a salt thereof wherein the reaction is carried out in the presence of water, or in the presence of a mixture of water and a water-miscible solvent;
  b) reaction of the resulting AZD9291 Aniline or a salt thereof with acryloyl chloride or 3-chloropropanoyl chloride, and where necessary, treatment with base to form AZD9291; and
  c) optional formation of a pharmaceutical acceptable salt thereof.

In a further aspect of the present disclosure, there is provided an improved process for the manufacture of AZD9291 or a pharmaceutically acceptable salt thereof which comprises:
  a) reaction of AZD9291 Nitrodiamine or a salt thereof with hydrogen, in the presence of a palladium(0)- and/or platinum(0)-based catalyst, and in the presence of an acid wherein the acid comprises an acid selected from $(C_{1-7}$hydrocarbyl$)$COOH, formic acid, trichloroacetic acid, trifluoroacetic acid, methanesulfonic acid, benzenesulfonic acid, p-toluenesulfonic acid, hydrochloric acid, sulfuric acid and phosphoric acid, to form AZD9291 Aniline or a salt thereof wherein the reaction is carried out in the presence of water, or in the presence of a mixture of water and a water-miscible solvent;
  b) reaction of the resulting AZD9291 Aniline or a salt thereof with acryloyl chloride or 3-chloropropanoyl chloride, and where necessary, treatment with base to form AZD9291; and
  c) optional formation of a pharmaceutical acceptable salt thereof.

In a further aspect of the present disclosure, there is provided an improved process for the manufacture of AZD9291 or a pharmaceutically acceptable salt thereof which comprises:
  a) reaction of AZD9291 Nitrodiamine or a salt thereof with hydrogen, in the presence of a palladium(0)- and/or platinum(0)-based catalyst, and in the presence of an acid wherein the acid comprises an acid selected from acetic acid, trifluoroacetic acid, methanesulfonic acid, benzenesulfonic acid, hydrochloric acid, sulfuric acid and phosphoric acid, to form AZD9291 Aniline or a salt thereof wherein the reaction is carried out in the presence of water, or in the presence of a mixture of water and a water-miscible solvent;
  b) reaction of the resulting AZD9291 Aniline or a salt thereof with acryloyl chloride or 3-chloropropanoyl chloride, and where necessary, treatment with base to form AZD9291; and
  c) optional formation of a pharmaceutical acceptable salt thereof.

In a further aspect of the present disclosure, there is provided an improved process for the manufacture of AZD9291 or a pharmaceutically acceptable salt thereof which comprises:
  a) reaction of AZD9291 Nitrodiamine or a salt thereof with hydrogen, in the presence of a palladium(0)- and/or platinum(0)-based catalyst, and in the presence of at least 1.0 molar equivalents of acid wherein the acid comprises an acid selected from acetic acid, trifluoroacetic acid, methanesulfonic acid, benzenesulfonic acid, hydrochloric acid, sulfuric acid and phosphoric acid, to form AZD9291 Aniline or a salt thereof wherein the reaction is carried out in the presence of water, or in the presence of a mixture of water and a water-miscible solvent;
  b) reaction of the resulting AZD9291 Aniline or a salt thereof with acryloyl chloride or 3-chloropropanoyl chloride, and where necessary, treatment with base to form AZD9291; and
  c) optional formation of a pharmaceutical acceptable salt thereof.

In a further aspect of the present disclosure, there is provided an improved process for the manufacture of AZD9291 or a pharmaceutically acceptable salt thereof which comprises:
  a) reaction of AZD9291 Nitrodiamine or a salt thereof with hydrogen, in the presence of a palladium(0)- and/or platinum(0)-based catalyst, and in the presence of 1.0-2.0 molar equivalents of acid wherein the acid comprises an acid selected from acetic acid, trifluoroacetic acid, methanesulfonic acid, benzenesulfonic acid, hydrochloric acid, sulfuric acid and phosphoric acid, to form AZD9291 Aniline or a salt thereof wherein the reaction is carried out in the presence of water, or in the presence of a mixture of water and a water-miscible solvent;
  b) reaction of the resulting AZD9291 Aniline or a salt thereof with acryloyl chloride or 3-chloropropanoyl chloride, and where necessary, treatment with base to form AZD9291; and
  c) optional formation of a pharmaceutical acceptable salt thereof.

In a further aspect of the present disclosure, there is provided an improved process for the manufacture of AZD9291 or a pharmaceutically acceptable salt thereof which comprises:
  a) reaction of AZD9291 Nitrodiamine or a salt thereof with hydrogen, in the presence of a palladium(0)- and/or platinum(0)-based catalyst, and in the presence of 1.4-1.6 molar equivalents of acid wherein the acid comprises an acid selected from acetic acid, trifluoroacetic acid, methanesulfonic acid, benzenesulfonic acid, hydrochloric acid, sulfuric acid and phosphoric acid, to form AZD9291 Aniline or a salt thereof wherein the reaction is carried out in the presence of water, or in the presence of a mixture of water and a water-miscible solvent;
b) reaction of the resulting AZD9291 Aniline or a salt thereof with acryloyl chloride or 3-chloropropanoyl chloride, and where necessary, treatment with base to form AZD9291; and
c) optional formation of a pharmaceutical acceptable salt thereof.

In a further aspect of the present disclosure, there is provided an improved process for the manufacture of AZD9291 or a pharmaceutically acceptable salt thereof which comprises:
a) reaction of AZD9291 Nitrodiamine or a salt thereof with hydrogen, in the presence of a palladium(0)- and/or platinum(0)-based catalyst, and in the presence of 1.6 molar equivalents of acid wherein the acid comprises an acid selected from acetic acid, trifluoroacetic acid, methanesulfonic acid, benzenesulfonic acid, hydrochloric acid, sulfuric acid and phosphoric acid, to form AZD9291 Aniline or a salt thereof wherein the reaction is carried out in the presence of water, or in the presence of a mixture of water and a water-miscible solvent;
b) reaction of the resulting AZD9291 Aniline or a salt thereof with acryloyl chloride or 3-chloropropanoyl chloride, and where necessary, treatment with base to form AZD9291; and
c) optional formation of a pharmaceutical acceptable salt thereof.

In a further aspect of the present disclosure, there is provided an improved process for the manufacture of AZD9291 or a pharmaceutically acceptable salt thereof which comprises:
a) reaction of AZD9291 Nitrodiamine or a salt thereof with hydrogen, in the presence of a palladium(0)- and/or platinum(0)-based catalyst, and in the presence of 1.5 molar equivalents of acid wherein the acid comprises an acid selected from acetic acid, trifluoroacetic acid, methanesulfonic acid, benzenesulfonic acid, hydrochloric acid, sulfuric acid and phosphoric acid, to form AZD9291 Aniline or a salt thereof wherein the reaction is carried out in the presence of water, or in the presence of a mixture of water and a water-miscible solvent;
b) reaction of the resulting AZD9291 Aniline or a salt thereof with acryloyl chloride or 3-chloropropanoyl chloride, and where necessary, treatment with base to form AZD9291; and
c) optional formation of a pharmaceutical acceptable salt thereof.

In a further aspect of the present disclosure, there is provided an improved process for the manufacture of AZD9291 or a pharmaceutically acceptable salt thereof which comprises:
a) reaction of AZD9291 Nitrodiamine or a salt thereof with hydrogen, in the presence of a palladium(0)- and/or platinum(0)-based catalyst wherein the palladium(0)-based catalyst (if present) contains at least 0.0005 molar equivalents of palladium(0) and the platinum(0)-based catalyst (if present) contains at least 0.0001 molar equivalents of platinum(O), and in the presence of at least 1 molar equivalents of acid to form AZD9291 Aniline or a salt thereof wherein the reaction is carried out in the presence of water, or in the presence of a mixture of water and a water-miscible solvent;
b) reaction of the resulting AZD9291 Aniline or a salt thereof with acryloyl chloride or 3-chloropropanoyl chloride, and where necessary, treatment with base to form AZD9291; and
c) optional formation of a pharmaceutical acceptable salt thereof.

In a further aspect of the present disclosure, there is provided an improved process for the manufacture of AZD9291 or a pharmaceutically acceptable salt thereof which comprises:
d) reaction of AZD9291 Nitrodiamine or a salt thereof with hydrogen, in the presence of a palladium(0)- and/or platinum(0)-based catalyst wherein the palladium(0)-based catalyst (if present) contains at least 0.005 molar equivalents of palladium(0) and the platinum(0)-based catalyst (if present) contains at least 0.001 molar equivalents of platinum(0), and in the presence of at least 1 molar equivalents of acid to form AZD9291 Aniline or a salt thereof wherein the reaction is carried out in the presence of water, or in the presence of a mixture of water and a water-miscible solvent;
e) reaction of the resulting AZD9291 Aniline or a salt thereof with acryloyl chloride or 3-chloropropanoyl chloride, and where necessary, treatment with base to form AZD9291; and
f) optional formation of a pharmaceutical acceptable salt thereof.

In a further aspect of the present disclosure, there is provided an improved process for the manufacture of AZD9291 or a pharmaceutically acceptable salt thereof which comprises:
a) reaction of AZD9291 Nitrodiamine or a salt thereof with hydrogen, in the presence of a palladium(0)- and/or platinum(0)-based catalyst wherein the palladium(0)-based catalyst (if present) contains 0.005 molar equivalents of palladium(0) and the platinum(0)-based catalyst (if present) contains 0.001 molar equivalents of platinum(0), and in the presence of 1.5 molar equivalents of acid wherein the acid comprises an acid selected from acetic acid, trifluoroacetic acid, methanesulfonic acid, benzenesulfonic acid, hydrochloric acid, sulfuric acid and phosphoric acid, to form AZD9291 Aniline or a salt thereof wherein the reaction is carried out in the presence of water, or in the presence of a mixture of water and a water-miscible solvent;
b) reaction of the resulting AZD9291 Aniline or a salt thereof with acryloyl chloride or 3-chloropropanoyl chloride, and where necessary, treatment with base to form AZD9291; and
c) optional formation of a pharmaceutical acceptable salt thereof.

In a further aspect of the present disclosure, there is provided an improved process for the manufacture of AZD9291 or a pharmaceutically acceptable salt thereof which comprises:
a) reaction of AZD9291 Nitrodiamine or a salt thereof with hydrogen, in the presence of a platinum(0)-based catalyst, and in the presence of an acid wherein the acid comprises an acid selected from acetic acid, trifluoroacetic acid, methanesulfonic acid, benzenesulfonic acid, hydrochloric acid, sulfuric acid and phosphoric acid, to form AZD9291 Aniline or a salt thereof wherein the reaction is carried out in the presence of water, or in the presence of a mixture of water and a water-miscible solvent;
b) reaction of the resulting AZD9291 Aniline or a salt thereof with acryloyl chloride or 3-chloropropanoyl chloride, and where necessary, treatment with base to form AZD9291; and
c) optional formation of a pharmaceutical acceptable salt thereof.

In a further aspect of the present disclosure, there is provided an improved process for the manufacture of AZD9291 or a pharmaceutically acceptable salt thereof which comprises:
a) reaction of AZD9291 Nitrodiamine or a salt thereof with hydrogen, in the presence of a palladium(0)-based catalyst, and in the presence of an acid wherein the acid comprises an acid selected from acetic acid, trifluoroacetic acid, methanesulfonic acid, benzenesulfonic acid, hydrochloric acid, sulfuric acid and phosphoric acid, to form AZD9291 Aniline or a salt thereof wherein the reaction is carried out in the presence of water, or in the presence of a mixture of water and a water-miscible solvent;
b) reaction of the resulting AZD9291 Aniline or a salt thereof with acryloyl chloride or 3-chloropropanoyl chloride, and where necessary, treatment with base to form AZD9291; and
c) optional formation of a pharmaceutical acceptable salt thereof.

In a further aspect of the present disclosure, there is provided an improved process for the manufacture of AZD9291 or a pharmaceutically acceptable salt thereof which comprises:
a) reaction of AZD9291 Nitrodiamine or a salt thereof with hydrogen, in the presence of a palladium(0)-based catalyst, and in the presence of at least 1.0 molar equivalents of acid wherein the acid comprises an acid selected from acetic acid, trifluoroacetic acid, methanesulfonic acid, benzenesulfonic acid, hydrochloric acid, sulfuric acid and phosphoric acid, to form AZD9291 Aniline or a salt thereof wherein the reaction is carried out in the presence of water, or in the presence of a mixture of water and a water-miscible solvent;
b) reaction of the resulting AZD9291 Aniline or a salt thereof with acryloyl chloride or 3-chloropropanoyl chloride, and where necessary, treatment with base to form AZD9291; and
c) optional formation of a pharmaceutical acceptable salt thereof.

In a further aspect of the present disclosure, there is provided an improved process for the manufacture of AZD9291 or a pharmaceutically acceptable salt thereof which comprises:
a) reaction of AZD9291 Nitrodiamine or a salt thereof with hydrogen, in the presence of a palladium(0)-based catalyst, and in the presence of 1.0-2.0 molar equivalents of acid wherein the acid comprises an acid selected from acetic acid, trifluoroacetic acid, methanesulfonic acid, benzenesulfonic acid, hydrochloric acid, sulfuric acid and phosphoric acid, to form AZD9291 Aniline or a salt thereof wherein the reaction is carried out in the presence of water, or in the presence of a mixture of water and a water-miscible solvent;
b) reaction of the resulting AZD9291 Aniline or a salt thereof with acryloyl chloride or 3-chloropropanoyl chloride, and where necessary, treatment with base to form AZD9291; and
c) optional formation of a pharmaceutical acceptable salt thereof.

In a further aspect of the present disclosure, there is provided an improved process for the manufacture of AZD9291 or a pharmaceutically acceptable salt thereof which comprises:
a) reaction of AZD9291 Nitrodiamine or a salt thereof with hydrogen, in the presence of a palladium(0)-based catalyst, and in the presence of 1.4-1.6 molar equivalents of acid wherein the acid comprises an acid selected from acetic acid, trifluoroacetic acid, methanesulfonic acid, benzenesulfonic acid, hydrochloric acid, sulfuric acid and phosphoric acid, to form AZD9291 Aniline or a salt thereof wherein the reaction is carried out in the presence of water, or in the presence of a mixture of water and a water-miscible solvent;
b) reaction of the resulting AZD9291 Aniline or a salt thereof with acryloyl chloride or 3-chloropropanoyl chloride, and where necessary, treatment with base to form AZD9291; and
c) optional formation of a pharmaceutical acceptable salt thereof.

In a further aspect of the present disclosure, there is provided an improved process for the manufacture of AZD9291 or a pharmaceutically acceptable salt thereof which comprises:
a) reaction of AZD9291 Nitrodiamine or a salt thereof with hydrogen, in the presence of a palladium(0)-based catalyst, and in the presence of 1.6 molar equivalents of acid wherein the acid comprises an acid selected from acetic acid, trifluoroacetic acid, methanesulfonic acid, benzenesulfonic acid, hydrochloric acid, sulfuric acid and phosphoric acid, to form AZD9291 Aniline or a salt thereof wherein the reaction is carried out in the presence of water, or in the presence of a mixture of water and a water-miscible solvent;
b) reaction of the resulting AZD9291 Aniline or a salt thereof with acryloyl chloride or 3-chloropropanoyl chloride, and where necessary, treatment with base to form AZD9291; and
c) optional formation of a pharmaceutical acceptable salt thereof.

In a further aspect of the present disclosure, there is provided an improved process for the manufacture of AZD9291 or a pharmaceutically acceptable salt thereof which comprises:
a) reaction of AZD9291 Nitrodiamine or a salt thereof with hydrogen, in the presence of a palladium(0)-based catalyst, and in the presence of 1.5 molar equivalents of acid wherein the acid comprises an acid is selected from acetic acid, trifluoroacetic acid, methanesulfonic acid, benzenesulfonic acid, hydrochloric acid, sulfuric acid and phosphoric acid, to form AZD9291 Aniline or a salt thereof wherein the reaction is carried out in the presence of water, or in the presence of a mixture of water and a water-miscible solvent;
b) reaction of the resulting AZD9291 Aniline or a salt thereof with acryloyl chloride or 3-chloropropanoyl chloride, and where necessary, treatment with base to form AZD9291; and
c) optional formation of a pharmaceutical acceptable salt thereof.

In a further aspect of the present disclosure, there is provided an improved process for the manufacture of AZD9291 or a pharmaceutically acceptable salt thereof which comprises:

a) reaction of AZD9291 Nitrodiamine or a salt thereof with hydrogen, in the presence of a platinum(0)-based catalyst, and in the presence of at least 1.0 molar equivalents of acid wherein the acid comprises an acid selected from acetic acid, trifluoroacetic acid, methanesulfonic acid, benzenesulfonic acid, hydrochloric acid, sulfuric acid and phosphoric acid, to form AZD9291 Aniline or a salt thereof wherein the reaction is carried out in the presence of water, or in the presence of a mixture of water and a water-miscible solvent;
b) reaction of the resulting AZD9291 Aniline or a salt thereof with acryloyl chloride or 3-chloropropanoyl chloride, and where necessary, treatment with base to form AZD9291; and
c) optional formation of a pharmaceutical acceptable salt thereof.

In a further aspect of the present disclosure, there is provided an improved process for the manufacture of AZD9291 or a pharmaceutically acceptable salt thereof which comprises:
a) reaction of AZD9291 Nitrodiamine or a salt thereof with hydrogen, in the presence of a platinum(0)-based catalyst, and in the presence of 1.0-2.0 molar equivalents of acid wherein the acid comprises an acid selected from acetic acid, trifluoroacetic acid, methanesulfonic acid, benzenesulfonic acid, hydrochloric acid, sulfuric acid and phosphoric acid, to form AZD9291 Aniline or a salt thereof wherein the reaction is carried out in the presence of water, or in the presence of a mixture of water and a water-miscible solvent;
b) reaction of the resulting AZD9291 Aniline or a salt thereof with acryloyl chloride or 3-chloropropanoyl chloride, and where necessary, treatment with base to form AZD9291; and
c) optional formation of a pharmaceutical acceptable salt thereof.

In a further aspect of the present disclosure, there is provided an improved process for the manufacture of AZD9291 or a pharmaceutically acceptable salt thereof which comprises:
a) reaction of AZD9291 Nitrodiamine or a salt thereof with hydrogen, in the presence of a platinum(0)-based catalyst, and in the presence of 1.4-1.6 molar equivalents of acid wherein the acid comprises an acid selected from acetic acid, trifluoroacetic acid, methanesulfonic acid, benzenesulfonic acid, hydrochloric acid, sulfuric acid and phosphoric acid, to form AZD9291 Aniline or a salt thereof wherein the reaction is carried out in the presence of water, or in the presence of a mixture of water and a water-miscible solvent;
b) reaction of the resulting AZD9291 Aniline or a salt thereof with acryloyl chloride or 3-chloropropanoyl chloride, and where necessary, treatment with base to form AZD9291; and
c) optional formation of a pharmaceutical acceptable salt thereof.

In a further aspect of the present disclosure, there is provided an improved process for the manufacture of AZD9291 or a pharmaceutically acceptable salt thereof which comprises:
a) reaction of AZD9291 Nitrodiamine or a salt thereof with hydrogen, in the presence of a platinum(0)-based catalyst, and in the presence of 1.6 molar equivalents of acid wherein the acid comprises an acid selected from acetic acid, trifluoroacetic acid, methanesulfonic acid, benzenesulfonic acid, hydrochloric acid, sulfuric acid and phosphoric acid, to form AZD9291 Aniline or a salt thereof wherein the reaction is carried out in the presence of water, or in the presence of a mixture of water and a water-miscible solvent;
b) reaction of the resulting AZD9291 Aniline or a salt thereof with acryloyl chloride or 3-chloropropanoyl chloride, and where necessary, treatment with base to form AZD9291; and
c) optional formation of a pharmaceutical acceptable salt thereof.

In a further aspect of the present disclosure, there is provided an improved process for the manufacture of AZD9291 or a pharmaceutically acceptable salt thereof which comprises:
a) reaction of AZD9291 Nitrodiamine or a salt thereof with hydrogen, in the presence of a platinum(0)-based catalyst, and in the presence of 1.5 molar equivalents of acid wherein the acid comprises an acid selected from acetic acid, trifluoroacetic acid, methanesulfonic acid, benzenesulfonic acid, hydrochloric acid, sulfuric acid and phosphoric acid, to form AZD9291 Aniline or a salt thereof wherein the reaction is carried out in the presence of water, or in the presence of a mixture of water and a water-miscible solvent;
b) reaction of the resulting AZD9291 Aniline or a salt thereof with acryloyl chloride or 3-chloropropanoyl chloride, and where necessary, treatment with base to form AZD9291; and
c) optional formation of a pharmaceutical acceptable salt thereof.

In a further aspect of the present disclosure, there is provided an improved process for the manufacture of AZD9291 or a pharmaceutically acceptable salt thereof which comprises:
a) reaction of AZD9291 Nitrodiamine or a salt thereof with hydrogen, in the presence of a palladium(0)- and/or platinum(0)-based catalyst, and in the presence of an acid wherein the acid comprises methanesulfonic acid, to form AZD9291 Aniline wherein the reaction is carried out in the presence of water, or in the presence of a mixture of water and a water-miscible solvent;
b) reaction of the resulting AZD9291 Aniline or a salt thereof with acryloyl chloride or 3-chloropropanoyl chloride, and where necessary, treatment with base to form AZD9291; and
c) optional formation of a pharmaceutical acceptable salt thereof.

In a further aspect of the present disclosure, there is provided an improved process for the manufacture of AZD9291 or a pharmaceutically acceptable salt thereof which comprises:
a) reaction of AZD9291 Nitrodiamine or a salt thereof with hydrogen, in the presence of a palladium(0)- and/or platinum(0)-based catalyst, and in the presence of at least 1.0 molar equivalents of acid wherein the acid comprises methanesulfonic acid, to form AZD9291 Aniline or a salt thereof wherein the reaction is carried out in the presence of water, or in the presence of a mixture of water and a water-miscible solvent;
b) reaction of the resulting AZD9291 Aniline or a salt thereof with acryloyl chloride or 3-chloropropanoyl chloride, and where necessary, treatment with base to form AZD9291; and
c) optional formation of a pharmaceutical acceptable salt thereof.

In a further aspect of the present disclosure, there is provided an improved process for the manufacture of AZD9291 or a pharmaceutically acceptable salt thereof which comprises:
  a) reaction of AZD9291 Nitrodiamine or a salt thereof with hydrogen, in the presence of a platinum(0)-based catalyst, and in the presence of an acid wherein the acid comprises methanesulfonic acid, to form AZD9291 Aniline or a salt thereof wherein the reaction is carried out in the presence of water, or in the presence of a mixture of water and a water-miscible solvent;
  b) reaction of the resulting AZD9291 Aniline or a salt thereof with acryloyl chloride or 3-chloropropanoyl chloride, and where necessary, treatment with base to form AZD9291; and
  c) optional formation of a pharmaceutical acceptable salt thereof.

In a further aspect of the present disclosure, there is provided an improved process for the manufacture of AZD9291 or a pharmaceutically acceptable salt thereof which comprises:
  a) reaction of AZD9291 Nitrodiamine or a salt thereof with hydrogen, in the presence of a palladium(0)-based catalyst, and in the presence an acid wherein the acid comprises methanesulfonic acid, to form AZD9291 Aniline or a salt thereof wherein the reaction is carried out in the presence of water, or in the presence of a mixture of water and a water-miscible solvent;
  b) reaction of the resulting AZD9291 Aniline or a salt thereof with acryloyl chloride or 3-chloropropanoyl chloride, and where necessary, treatment with base to form AZD9291; and
  c) optional formation of a pharmaceutical acceptable salt thereof.

In a further aspect of the present disclosure, there is provided an improved process for the manufacture of AZD9291 or a pharmaceutically acceptable salt thereof which comprises:
  a) reaction of AZD9291 Nitrodiamine or a salt thereof with hydrogen, in the presence of a palladium(0)- and/or platinum(0)-based catalyst, and in the presence of an acid wherein the acid comprises methanesulfonic acid, to form AZD9291 Aniline or a salt thereof wherein the reaction is carried out in the presence of a mixture of water and a water-miscible solvent;
  b) reaction of the resulting AZD9291 Aniline or a salt thereof with acryloyl chloride or 3-chloropropanoyl chloride, and where necessary, treatment with base to form AZD9291; and
  c) optional formation of a pharmaceutical acceptable salt thereof.

In a further aspect of the present disclosure, there is provided an improved process for the manufacture of AZD9291 or a pharmaceutically acceptable salt thereof which comprises:
  a) reaction of AZD9291 Nitrodiamine or a salt thereof with hydrogen, in the presence of a palladium(0)- and/or platinum(0)-based catalyst, and in the presence of at least 1.0 molar equivalents of acid wherein the acid comprises methanesulfonic acid, to form AZD9291 Aniline or a salt thereof wherein the reaction is carried out in the presence of a mixture of water and a water-miscible solvent;
  b) reaction of the resulting AZD9291 Aniline or a salt thereof with acryloyl chloride or 3-chloropropanoyl chloride, and where necessary, treatment with base to form AZD9291; and
  c) optional formation of a pharmaceutical acceptable salt thereof.

In a further aspect of the present disclosure, there is provided an improved process for the manufacture of AZD9291 or a pharmaceutically acceptable salt thereof which comprises:
  a) reaction of AZD9291 Nitrodiamine or a salt thereof with hydrogen, in the presence of a palladium(0)- and/or platinum(0)-based catalyst, and in the presence of at least 1.0 molar equivalents of acid wherein the acid comprises methanesulfonic acid, to form AZD9291 Aniline or a salt thereof wherein the reaction is carried out in the presence of a mixture of water and a water-miscible solvent wherein the water-miscible solvent is selected from an alcohol, tetrahydrofuran, acetonitrile, dimethyl sulfoxide and N-methylpyrrolidin-2-one;
  b) reaction of the resulting AZD9291 Aniline or a salt thereof with acryloyl chloride or 3-chloropropanoyl chloride, and where necessary, treatment with base to form AZD9291; and
  c) optional formation of a pharmaceutical acceptable salt thereof.

In a further aspect of the present disclosure, there is provided an improved process for the manufacture of AZD9291 or a pharmaceutically acceptable salt thereof which comprises:
  a) reaction of AZD9291 Nitrodiamine or a salt thereof with hydrogen, in the presence of a palladium(0)- and/or platinum(0)-based catalyst, and in the presence of an acid wherein the acid comprises an acid selected from acetic acid, trifluoroacetic acid, methanesulfonic acid, benzenesulfonic acid, hydrochloric acid, sulfuric acid and phosphoric acid, to form AZD9291 Aniline or a salt thereof wherein the reaction is carried out in the presence of water, or in the presence of a mixture of water and a water-miscible solvent wherein the water-miscible solvent is selected from ($C_{1-6}$alkyl)-OH, tetrahydrofuran, acetonitrile, dimethyl sulfoxide, dimethylformamide, dimethylacetamide and N-methylpyrrolidin-2-one;
  b) reaction of the resulting AZD9291 Aniline or a salt thereof with acryloyl chloride or 3-chloropropanoyl chloride, and where necessary, treatment with base to form AZD9291; and
  c) optional formation of a pharmaceutical acceptable salt thereof.

In a further aspect of the present disclosure, there is provided an improved process for the manufacture of AZD9291 or a pharmaceutically acceptable salt thereof which comprises:
  a) reaction of AZD9291 Nitrodiamine or a salt thereof with hydrogen, in the presence of a palladium(0)- and/or platinum(0)-based catalyst, and in the presence of at least 1.0 molar equivalents of acid wherein the acid comprises methanesulfonic acid, to form AZD9291 Aniline or a salt thereof wherein the reaction is carried out in the presence of a mixture of water and a water-miscible solvent wherein the water-miscible solvent is selected from ($C_{1-6}$alkyl)-OH, tetrahydrofuran, acetonitrile, dimethyl sulfoxide, dimethylformamide, dimethylacetamide and N-methylpyrrolidin-2-one;
  b) reaction of the resulting AZD9291 Aniline or a salt thereof with acryloyl chloride or 3-chloropropanoyl chloride, and where necessary, treatment with base to form AZD9291; and c) optional formation of a pharmaceutical acceptable salt thereof.

In a further aspect of the present disclosure, there is provided an improved process for the manufacture of AZD9291 or a pharmaceutically acceptable salt thereof which comprises:
a) reaction of AZD9291 Nitrodiamine or a salt thereof with hydrogen in the presence of a palladium(0)- and/or platinum(0)-based catalyst, and in the presence of at least 1.0 molar equivalents of acid wherein the acid comprises methanesulfonic acid, to form AZD9291 Aniline or a salt thereof wherein the reaction is carried out in the presence of a mixture of water and a water-miscible solvent wherein the water-miscible solvent is selected from methanol, ethanol, propanol, tetrahydrofuran, acetonitrile, dimethyl sulfoxide, dimethylformamide, dimethylacetamide and N-methylpyrrolidin-2-one;
b) reaction of the resulting AZD9291 Aniline or a salt thereof with acryloyl chloride or 3-chloropropanoyl chloride, and where necessary, treatment with base to form AZD9291; and
c) optional formation of a pharmaceutical acceptable salt thereof.

In a further aspect of the present disclosure, there is provided an improved process for the manufacture of AZD9291 or a pharmaceutically acceptable salt thereof which comprises:
a) reaction of AZD9291 Nitrodiamine or a salt thereof with hydrogen, in the presence of a palladium(0)- and/or platinum(0)-based catalyst, and in the presence of at least 1.0 molar equivalents of acid wherein the acid comprises methanesulfonic acid, to form AZD9291 Aniline or a salt thereof wherein the reaction is carried out in the presence of a mixture of water and a water-miscible solvent wherein the water-miscible solvent is selected from methanol, ethanol, n-propanol, isopropanol, tetrahydrofuran, acetonitrile, dimethyl sulfoxide, dimethylformamide, dimethylacetamide and N-methylpyrrolidin-2-one;
b) reaction of the resulting AZD9291 Aniline or a salt thereof with acryloyl chloride or 3-chloropropanoyl chloride, and where necessary, treatment with base to form AZD9291; and
c) optional formation of a pharmaceutical acceptable salt thereof.

In a further aspect of the present disclosure, there is provided an improved process for the manufacture of AZD9291 or a pharmaceutically acceptable salt thereof which comprises:
a) reaction of AZD9291 Nitrodiamine or a salt thereof with hydrogen, in the presence of a palladium(0)- and/or platinum(0)-based catalyst, and in the presence of at least 1.0 molar equivalents of acid wherein the acid comprises methanesulfonic acid, to form AZD9291 Aniline or a salt thereof wherein the reaction is carried out in the presence of a mixture of water and a water-miscible solvent wherein the water-miscible solvent is selected from methanol, isopropanol, tetrahydrofuran, acetonitrile, dimethyl sulfoxide and N-methylpyrrolidin-2-one;
b) reaction of the resulting AZD9291 Aniline or a salt thereof with acryloyl chloride or 3-chloropropanoyl chloride, and where necessary, treatment with base to form AZD9291; and
c) optional formation of a pharmaceutical acceptable salt thereof.

In a further aspect of the present disclosure, there is provided an improved process for the manufacture of AZD9291 or a pharmaceutically acceptable salt thereof which comprises:
a) reaction of AZD9291 Nitrodiamine or a salt thereof with hydrogen, in the presence of a palladium(0)- and/or platinum(0)-based catalyst, and in the presence of an acid wherein the acid comprises methanesulfonic acid, to form AZD9291 Aniline or a salt thereof wherein the reaction is carried out in the presence of water;
b) reaction of the resulting AZD9291 Aniline or a salt thereof with acryloyl chloride or 3-chloropropanoyl chloride, and where necessary, treatment with base to form AZD9291; and
c) optional formation of a pharmaceutical acceptable salt thereof.

In a further aspect of the present disclosure, there is provided an improved process for the manufacture of AZD9291 or a pharmaceutically acceptable salt thereof which comprises:
a) reaction of AZD9291 Nitrodiamine or a salt thereof with hydrogen, in the presence of a palladium(0)- and/or platinum(0)-based catalyst, and in the presence of at least 1.0 molar equivalents of acid wherein the acid comprises methanesulfonic acid, to form AZD9291 Aniline or a salt thereof wherein the reaction is carried out in the presence of water;
b) reaction of the resulting AZD9291 Aniline or a salt thereof with acryloyl chloride or 3-chloropropanoyl chloride, and where necessary, treatment with base to form AZD9291; and
c) optional formation of a pharmaceutical acceptable salt thereof.

In a further aspect of the present disclosure, there is provided an improved process for the manufacture of AZD9291 or a pharmaceutically acceptable salt thereof which comprises:
a) reaction of AZD9291 Nitrodiamine or a salt thereof with hydrogen, in the presence of a palladium(0)- and/or platinum(0)-based catalyst, and in the presence of 1.4-1.6 molar equivalents of acid wherein the acid comprises an selected from acetic acid, trifluoroacetic acid, methanesulfonic acid, benzenesulfonic acid, hydrochloric acid, sulfuric acid and phosphoric acid, to form AZD9291 Aniline or a salt thereof wherein the reaction is carried out in the presence of water;
b) reaction of the resulting AZD9291 Aniline or a salt thereof with acryloyl chloride or 3-chloropropanoyl chloride, and where necessary, treatment with base to form AZD9291; and
c) optional formation of a pharmaceutical acceptable salt thereof.

In a further aspect of the present disclosure, there is provided an improved process for the manufacture of AZD9291 or a pharmaceutically acceptable salt thereof which comprises:
a) reaction of AZD9291 Nitrodiamine or a salt thereof with hydrogen, in the presence of a palladium(0)- and/or platinum(0)-based catalyst wherein the palladium(0)-based catalyst (if present) contains 0.005 molar equivalents of palladium(0) and the platinum(0)-based catalyst (if present) contains 0.001 molar equivalents of platinum(0), and in the presence of 1.5 molar equivalents of acid wherein the acid comprises an acid selected from acetic acid, trifluoroacetic acid, methanesulfonic acid, benzenesulfonic acid, hydrochloric acid, sulfuric acid and phosphoric acid, to form AZD9291 Aniline or a salt thereof wherein the reaction is carried out in the presence of water;
  b) reaction of the resulting AZD9291 Aniline or a salt thereof with acryloyl chloride or 3-chloropropanoyl chloride, and where necessary, treatment with base to form AZD9291; and
  c) optional formation of a pharmaceutical acceptable salt thereof.

In a further aspect of the present disclosure, there is provided an improved process for the manufacture of AZD9291 or a pharmaceutically acceptable salt thereof which comprises:
  a) reaction of AZD9291 Nitrodiamine or a salt thereof with hydrogen in the presence of a palladium(0)- and/or platinum(0)-based catalyst, and in the presence of 1.4-1.6 molar equivalents of acid wherein the acid comprises an acid selected from acetic acid, trifluoroacetic acid, methanesulfonic acid, benzenesulfonic acid, hydrochloric acid, sulfuric acid and phosphoric acid, to form AZD9291 Aniline or a salt thereof wherein the reaction is carried out in the presence of a mixture of water and a water-miscible solvent;
  b) reaction of the resulting AZD9291 Aniline or a salt thereof with acryloyl chloride or 3-chloropropanoyl chloride, and where necessary, treatment with base to form AZD9291; and
  c) optional formation of a pharmaceutical acceptable salt thereof.

In a further aspect of the present disclosure, there is provided an improved process for the manufacture of AZD9291 or a pharmaceutically acceptable salt thereof which comprises:
  a) reaction of AZD9291 Nitrodiamine or a salt thereof with hydrogen, in the presence a palladium(0)- and/or platinum(0)-based catalyst wherein the palladium(0)-based catalyst (if present) contains 0.005 molar equivalents of palladium(0) and the platinum(0)-based catalyst (if present) contains 0.001 molar equivalents of a platinum(0), and in the presence of 1.5 molar equivalents of acid wherein the acid comprises an acid selected from acetic acid, trifluoroacetic acid, methanesulfonic acid, benzenesulfonic acid, hydrochloric acid, sulfuric acid and phosphoric acid, to form AZD9291 Aniline or a salt thereof wherein the reaction is carried out in the presence of in the presence of a mixture of water and a water-miscible solvent;
  b) reaction of the resulting AZD9291 Aniline or a salt thereof with acryloyl chloride or 3-chloropropanoyl chloride, and where necessary, treatment with base to form AZD9291; and
  c) optional formation of a pharmaceutical acceptable salt thereof.

In a further aspect of the present disclosure, there is provided an improved process for the manufacture of AZD9291 or a pharmaceutically acceptable salt thereof which comprises:
  a) reaction of AZD9291 Nitrodiamine or a salt thereof with hydrogen, in the presence of a palladium(0)- and/or platinum(0)-based catalyst, and in the presence of 1.4-1.6 molar equivalents of acid wherein the acid comprises an acid selected from acetic acid, trifluoroacetic acid, methanesulfonic acid, benzenesulfonic acid, hydrochloric acid, sulfuric acid and phosphoric acid, to form AZD9291 Aniline or a salt thereof wherein the reaction is carried out in the presence of a mixture of water and a water-miscible solvent wherein the water-miscible solvent is selected from methanol, isopropanol, tetrahydrofuran, acetonitrile, dimethyl sulfoxide and N-methylpyrrolidin-2-one;
  b) reaction of the resulting AZD9291 Aniline or a salt thereof with acryloyl chloride or 3-chloropropanoyl chloride, and where necessary, treatment with base to form AZD9291; and
  c) optional formation of a pharmaceutical acceptable salt thereof.

In a further aspect of the present disclosure, there is provided an improved process for the manufacture of AZD9291 or a pharmaceutically acceptable salt thereof which comprises:
  a) reaction of AZD9291 Nitrodiamine or a salt thereof with hydrogen, in the presence of a palladium(0)- and/or platinum(0)-based catalyst wherein the palladium(0)-based catalyst (if present) contains 0.005 molar equivalents of palladium(0) or the platinum(0)-based catalyst (if present) contains 0.001 molar equivalents of platinum(0), and in the presence of 1.5 molar equivalents of acid wherein the acid comprise an acid selected from acetic acid, trifluoroacetic acid, methanesulfonic acid, benzenesulfonic acid, hydrochloric acid, sulfuric acid and phosphoric acid, to form AZD9291 Aniline or a salt thereof wherein the reaction is carried out in the presence of in the presence of a mixture of water and a water-miscible solvent wherein the water-miscible solvent is selected from methanol, isopropanol, tetrahydrofuran, acetonitrile, dimethyl sulfoxide and N-methylpyrrolidin-2-one;
  b) reaction of the resulting AZD9291 Aniline or a salt thereof with acryloyl chloride or 3-chloropropanoyl chloride, and where necessary, treatment with base to form AZD9291; and
  c) optional formation of a pharmaceutical acceptable salt thereof.

In a further aspect of the present disclosure, there is provided an improved process for the manufacture of AZD9291 or a mesylate salt thereof which comprises: a) reaction of AZD9291 Nitrodiamine or a salt thereof with hydrogen, in the
  presence of a platinum(0)-based catalyst, and in the presence of 1.4-1.6 molar equivalents of acid wherein the acid comprises methanesulfonic acid, to form AZD9291 Aniline or a salt thereof wherein the reaction is carried out in the presence of water, or in the presence of a mixture of water and a water-miscible solvent;
  b) reaction of the resulting AZD9291 Aniline or a salt thereof with acryloyl chloride or 3-chloropropanoyl chloride, and where necessary, treatment with base to form AZD9291; and
  c) optional formation of a mesylate salt.

In a further aspect of the present disclosure, there is provided an improved process for the manufacture of AZD9291 or a mesylate salt thereof which comprises:
  a) reaction of AZD9291 Nitrodiamine or a salt thereof with hydrogen, in the presence of a platinum(0)-based catalyst, and in the presence of 1.5 molar equivalents of acid wherein the acid comprises methanesulfonic acid, to form AZD9291 Aniline or a salt thereof wherein the reaction is carried out in the presence of water, or in the presence of a mixture of water and a water-miscible solvent;

b) reaction of the resulting AZD9291 Aniline or a salt thereof with acryloyl chloride or 3-chloropropanoyl chloride, and where necessary, treatment with base to form AZD9291; and c) optional formation of a mesylate salt.

In a further aspect of the present disclosure, there is provided an improved process for the manufacture of AZD9291 or a mesylate salt thereof which comprises:

a) reaction of AZD9291 Nitrodiamine or a salt thereof with hydrogen, in the presence of a platinum(0)-based catalyst, and in the presence of 1.6 molar equivalents of acid wherein the acid comprise methanesulfonic acid, to form AZD9291 Aniline or a salt thereof wherein the reaction is carried out in the presence of water, or in the presence of a mixture of water and a water-miscible solvent;

b) reaction of the resulting AZD9291 Aniline or a salt thereof with acryloyl chloride or 3-chloropropanoyl chloride, and where necessary, treatment with base to form AZD9291; and c) optional formation of a mesylate salt.

In a further aspect of the present disclosure, there is provided an improved process for the manufacture of AZD9291 or a mesylate salt thereof which comprises:

a) reaction of AZD9291 Nitrodiamine or a salt thereof with hydrogen, in the presence of a platinum(0)-based catalyst wherein the platinum(0)-based catalyst contains at least 0.0001 molar equivalents of platinum(0), and in the presence of an acid wherein the acid comprises methanesulfonic acid, to form AZD9291 Aniline or a salt thereof wherein the reaction is carried out in the presence of water, or in the presence of a mixture of water and a water-miscible solvent;

b) reaction of the resulting AZD9291 Aniline or a salt thereof with acryloyl chloride or 3-chloropropanoyl chloride, and where necessary, treatment with base to form AZD9291; and c) optional formation of a mesylate salt.

In a further aspect of the present disclosure, there is provided an improved process for the manufacture of AZD9291 or a mesylate salt thereof which comprises:

a) reaction of AZD9291 Nitrodiamine or a salt thereof with hydrogen, in the presence of a platinum(0)-based catalyst wherein the platinum(0)-based catalyst contains 0.001 molar equivalents of platinum(0), and in the presence of an acid wherein the acid comprises methanesulfonic acid, to form AZD9291 Aniline or a salt thereof wherein the reaction is carried out in the presence of water, or in the presence of a mixture of water and a water-miscible solvent;

b) reaction of the resulting AZD9291 Aniline or a salt thereof with acryloyl chloride or 3-chloropropanoyl chloride, and where necessary, treatment with base to form AZD9291; and c) optional formation of a mesylate salt.

In a further aspect of the present disclosure, there is provided an improved process for the manufacture of AZD9291 or a mesylate salt thereof which comprises:

a) reaction of AZD9291 Nitrodiamine or a salt thereof with hydrogen, in the presence of a platinum(0)-based catalyst wherein the platinum(0)-based catalyst contains 0.001 molar equivalents of platinum(0), and in the presence of 1.5 molar equivalents of acid wherein the acid comprises methanesulfonic acid, to form AZD9291 Aniline or a salt thereof wherein the reaction is carried out in the presence of water, or in the presence of a mixture of water and a water-miscible solvent;

b) reaction of the resulting AZD9291 Aniline or a salt thereof with acryloyl chloride or 3-chloropropanoyl chloride, and where necessary, treatment with base to form AZD9291; and c) optional formation of a mesylate salt.

In a further aspect of the present disclosure, there is provided an improved process for the manufacture of AZD9291 or a mesylate salt thereof which comprises:

a) reaction of AZD9291 Nitrodiamine or a salt thereof with hydrogen, in the presence of a platinum(0)-based catalyst wherein the platinum(0)-based catalyst contains 0.001 molar equivalents of platinum(0), and in the presence of 1.5 molar equivalents of acid wherein the acid comprises methanesulfonic acid, to form AZD9291 Aniline or a salt thereof wherein the reaction is carried out in the presence of water;

b) reaction of the resulting AZD9291 Aniline or a salt thereof with acryloyl chloride or 3-chloropropanoyl chloride, and where necessary, treatment with base to form AZD9291; and c) optional formation of a mesylate salt.

In a further aspect of the present disclosure, there is provided an improved process for the manufacture of AZD9291 or a mesylate salt thereof which comprises:

a) reaction of AZD9291 Nitrodiamine or a salt thereof with hydrogen, in the presence of a platinum(0)-based catalyst wherein the platinum(0)-based catalyst contains 0.001 molar equivalents of platinum(0), and in the presence of 1.5 molar equivalents of acid wherein the acid comprises methanesulfonic acid, to form AZD9291 Aniline or a salt thereof wherein the reaction is carried out in the presence of a mixture of water and a water-miscible solvent;

b) reaction of the resulting AZD9291 Aniline or a salt thereof with acryloyl chloride or 3-chloropropanoyl chloride, and where necessary, treatment with base to form AZD9291; and c) optional formation of a mesylate salt.

In a further aspect of the present disclosure, there is provided an improved process for the manufacture of AZD9291 or a mesylate salt thereof which comprises:

a) reaction of AZD9291 Nitrodiamine or a salt thereof with hydrogen, in the presence of a platinum(0)-based catalyst wherein the platinum(0)-based catalyst contains 0.001 molar equivalents of platinum(0), and in the presence of 1.5 molar equivalents of acid wherein the acid comprises methanesulfonic acid, to form AZD9291 Aniline or a salt thereof wherein the reaction is carried out in the presence of a mixture of water and a water-miscible solvent wherein the water-miscible solvent is selected from methanol, isopropanol, tetrahydrofuran, acetonitrile, dimethyl sulfoxide and N-methylpyrrolidin-2-one;

b) reaction of the resulting AZD9291 Aniline or a salt thereof with acryloyl chloride or 3-chloropropanoyl chloride, and where necessary, treatment with base to form AZD9291; and c) optional formation of a mesylate salt.

In a further aspect of the present disclosure, there is provided an improved process for the manufacture of AZD9291 or a mesylate salt thereof which comprises:

a) reaction of AZD9291 Nitrodiamine or a salt thereof with hydrogen, in the presence of a platinum(0)-based catalyst wherein the platinum(0)-based catalyst contains 0.001 molar equivalents of platinum(0), and in the presence of 1.6 molar equivalents of acid wherein the acid comprises methanesulfonic acid, to form AZD9291 Aniline or a salt thereof wherein the reaction is carried out in the presence of water, or in the presence of a mixture of water and a water-miscible solvent;
  b) reaction of the resulting AZD9291 Aniline or a salt thereof with acryloyl chloride or 3-chloropropanoyl chloride, and where necessary, treatment with base to form AZD9291; and
  c) optional formation of a mesylate salt.

In a further aspect of the present disclosure, there is provided an improved process for the manufacture of AZD9291 or a mesylate salt thereof which comprises:
  a) reaction of AZD9291 Nitrodiamine or a salt thereof with hydrogen, in the presence of a platinum(0)-based catalyst wherein the platinum(0)-based catalyst contains 0.001 molar equivalents of platinum(0), and in the presence of 1.6 molar equivalents of acid wherein the acid comprises methanesulfonic acid, to form AZD9291 Aniline or a salt thereof wherein the reaction is carried out in the presence of water;
  b) reaction of the resulting AZD9291 Aniline or a salt thereof with acryloyl chloride or 3-chloropropanoyl chloride, and where necessary, treatment with base to form AZD9291; and
  c) optional formation of a mesylate salt.

In a further aspect of the present disclosure, there is provided an improved process for the manufacture of AZD9291 or a mesylate salt thereof which comprises:
  a) reaction of AZD9291 Nitrodiamine or a salt thereof with hydrogen, in the presence of a platinum(0)-based catalyst wherein the platinum(0)-based catalyst contains 0.001 molar equivalents of platinum(0), and in the presence of 1.6 molar equivalents of acid wherein the acid comprises methanesulfonic acid, to form AZD9291 Aniline or a salt thereof wherein the reaction is carried out in the presence of a mixture of water and a water-miscible solvent;
  b) reaction of the resulting AZD9291 Aniline or a salt thereof with acryloyl chloride or 3-chloropropanoyl chloride, and where necessary, treatment with base to form AZD9291; and
  c) optional formation of a mesylate salt.

In a further aspect of the present disclosure, there is provided an improved process for the manufacture of AZD9291 or a mesylate salt thereof which comprises:
  a) reaction of AZD9291 Nitrodiamine or a salt thereof with hydrogen, in the presence of a platinum(0)-based catalyst wherein the platinum(0)-based catalyst contains 0.001 molar equivalents of platinum(0), and in the presence of 1.6 molar equivalents of acid wherein the acid comprises methanesulfonic acid, to form AZD9291 Aniline or a salt thereof wherein the reaction is carried out in the presence of water, or in the presence of a mixture of water and a water-miscible solvent wherein the water-miscible solvent is selected from methanol, isopropanol, tetrahydrofuran, acetonitrile, dimethyl sulfoxide and N-methylpyrrolidin-2-one;
  b) reaction of the resulting AZD9291 Aniline or a salt thereof with acryloyl chloride or 3-chloropropanoyl chloride, and where necessary, treatment with base to form AZD9291; and
  c) optional formation of a mesylate salt.

In a further aspect of the present disclosure, there is provided an improved process for the manufacture of AZD9291 or a mesylate salt thereof which comprises:
  a) reaction of AZD9291 Nitrodiamine or a salt thereof with hydrogen, in the presence of a palladium(0)-based catalyst, and in the presence of 1.4-1.6 molar equivalents of acid wherein the acid comprises methanesulfonic acid, to form AZD9291 Aniline or a salt thereof wherein the reaction is carried out in the presence of water, or in the presence of a mixture of water and a water-miscible solvent;
  b) reaction of the resulting AZD9291 Aniline or a salt thereof with acryloyl chloride or 3-chloropropanoyl chloride, and where necessary, treatment with base to form AZD9291; and
  c) optional formation of a mesylate salt.

In a further aspect of the present disclosure, there is provided an improved process for the manufacture of AZD9291 or a mesylate salt thereof which comprises:
  a) reaction of AZD9291 Nitrodiamine or a salt thereof with hydrogen, in the presence of a palladium(0)-based catalyst, and in the presence of 1.5 molar equivalents of acid wherein the acid comprises methanesulfonic acid, to form AZD9291 Aniline or a salt thereof wherein the reaction is carried out in the presence of water, or in the presence of a mixture of water and a water-miscible solvent;
  b) reaction of the resulting AZD9291 Aniline or a salt thereof with acryloyl chloride or 3-chloropropanoyl chloride, and where necessary, treatment with base to form AZD9291; and
  c) optional formation of a mesylate salt.

In a further aspect of the present disclosure, there is provided an improved process for the manufacture of AZD9291 or a mesylate salt thereof which comprises:
  a) reaction of AZD9291 Nitrodiamine or a salt thereof with hydrogen, in the presence of a palladium(0)-based catalyst, and in the presence of 1.6 molar equivalents of acid wherein the acid comprises methanesulfonic acid, to form AZD9291 Aniline or a salt thereof wherein the reaction is carried out in the presence of water, or in the presence of a mixture of water and a water-miscible solvent;
  b) reaction of the resulting AZD9291 Aniline or a salt thereof with acryloyl chloride or 3-chloropropanoyl chloride, and where necessary, treatment with base to form AZD9291; and
  c) optional formation of a mesylate salt.

In a further aspect of the present disclosure, there is provided an improved process for the manufacture of AZD9291 or a mesylate salt thereof which comprises:
  a) reaction of AZD9291 Nitrodiamine or a salt thereof with hydrogen, in the presence of a palladium(0)-based catalyst wherein the palladium(0)-based catalyst contains at least 0.0005 molar equivalents of a palladium(0)-based catalyst, and in the presence of acid wherein the acid comprises methanesulfonic acid, to form AZD9291 Aniline or a salt thereof wherein the reaction is carried out in the presence of water, or in the presence of a mixture of water and a water-miscible solvent;
  b) reaction of the resulting AZD9291 Aniline or a salt thereof with acryloyl chloride or 3-chloropropanoyl chloride, and where necessary, treatment with base to form AZD9291; and
  c) optional formation of a mesylate salt.

In a further aspect of the present disclosure, there is provided an improved process for the manufacture of AZD9291 or a mesylate salt thereof which comprises:
  a) reaction of AZD9291 Nitrodiamine or a salt thereof with hydrogen, in the presence of a palladium(0)-based catalyst wherein the palladium(0)-based catalyst contains 0.005 molar equivalents of palladium(0), and in the presence of acid wherein the acid comprises methanesulfonic acid, to form AZD9291 Aniline or a salt thereof wherein the reaction is carried out in the presence of water, or in the presence of a mixture of water and a water-miscible solvent;
  b) reaction of the resulting AZD9291 Aniline or a salt thereof with acryloyl chloride or 3-chloropropanoyl chloride, and where necessary, treatment with base to form AZD9291; and
  c) optional formation of a mesylate salt.

In a further aspect of the present disclosure, there is provided an improved process for the manufacture of AZD9291 or a mesylate salt thereof which comprises:
  a) reaction of AZD9291 Nitrodiamine or a salt thereof with hydrogen, in the presence of a palladium(0)-based catalyst wherein the palladium(0)-based catalyst contains 0.005 molar equivalents of palladium(0), and in the presence of 1.5 molar equivalents of acid wherein the acid comprises methanesulfonic acid, to form AZD9291 Aniline or a salt thereof wherein the reaction is carried out in the presence of water, or in the presence of a mixture of water and a water-miscible solvent;
  b) reaction of the resulting AZD9291 Aniline or a salt thereof with acryloyl chloride or 3-chloropropanoyl chloride, and where necessary, treatment with base to form AZD9291; and
  c) optional formation of a mesylate salt.

In a further aspect of the present disclosure, there is provided an improved process for the manufacture of AZD9291 or a mesylate salt thereof which comprises:
  a) reaction of AZD9291 Nitrodiamine or a salt thereof with hydrogen, in the presence of a palladium(0)-based catalyst wherein the palladium(0)-based catalyst contains 0.005 molar equivalents of palladium(0), and in the presence of 1.5 molar equivalents of acid wherein the acid comprises methanesulfonic acid, to form AZD9291 Aniline or a salt thereof wherein the reaction is carried out in the presence of water;
  b) reaction of the resulting AZD9291 Aniline or a salt thereof with acryloyl chloride or 3-chloropropanoyl chloride, and where necessary, treatment with base to form AZD9291; and
  c) optional formation of a mesylate salt.

In a further aspect of the present disclosure, there is provided an improved process for the manufacture of AZD9291 or a mesylate salt thereof which comprises:
  a) reaction of AZD9291 Nitrodiamine or a salt thereof with hydrogen, in the presence of a palladium(0)-based catalyst wherein the palladium(0)-based catalyst contains 0.005 molar equivalents of palladium(0), and in the presence of 1.5 molar equivalents of acid wherein the acid comprises methanesulfonic acid, to form AZD9291 Aniline or a salt thereof wherein the reaction is carried out in the presence of a mixture of water and a water-miscible solvent;
  b) reaction of the resulting AZD9291 Aniline with acryloyl chloride or 3-chloropropanoyl chloride, and where necessary, treatment with base to form AZD9291; and
  c) optional formation of a mesylate salt.

In a further aspect of the present disclosure, there is provided an improved process for the manufacture of AZD9291 or a mesylate salt thereof which comprises:
  a) reaction of AZD9291 Nitrodiamine or a salt thereof with hydrogen, in the presence of a palladium(0)-based catalyst wherein the palladium(0)-based catalyst contains 0.005 molar equivalents of palladium(0), and in the presence of 1.5 molar equivalents of acid wherein the acid comprises methanesulfonic acid, to form AZD9291 Aniline or a salt thereof wherein the reaction is carried out in the presence of a mixture of water and a water-miscible solvent wherein the water-miscible solvent is selected from methanol, isopropanol, tetrahydrofuran, acetonitrile, dimethyl sulfoxide and N-methylpyrrolidin-2-one;
  b) reaction of the resulting AZD9291 Aniline with acryloyl chloride or 3-chloropropanoyl chloride, and where necessary, treatment with base to form AZD9291; and
  c) optional formation of a mesylate salt.

In a further aspect of the present disclosure, there is provided an improved process for the manufacture of AZD9291 or a mesylate salt thereof which comprises:
  a) reaction of AZD9291 Nitrodiamine or a salt thereof with hydrogen, in the presence of a palladium(0)-based catalyst wherein the palladium(0)-based catalyst contains 0.005 molar equivalents of palladium(0), and in the presence of 1.6 molar equivalents of acid wherein the acid comprises methanesulfonic acid, to form AZD9291 Aniline or a salt thereof wherein the reaction is carried out in the presence of water, or in the presence of a mixture of water and a water-miscible solvent;
  b) reaction of the resulting AZD9291 Aniline with acryloyl chloride or 3-chloropropanoyl chloride, and where necessary, treatment with base to form AZD9291; and
  c) optional formation of a mesylate salt.

In a further aspect of the present disclosure, there is provided an improved process for the manufacture of AZD9291 or a mesylate salt thereof which comprises:
  a) reaction of AZD9291 Nitrodiamine or a salt thereof with hydrogen, in the presence of a palladium(0)-based catalyst wherein the palladium(0)-based catalyst contains 0.005 molar equivalents of palladium(0), and in the presence of 1.6 molar equivalents of acid wherein the acid comprises methanesulfonic acid, to form AZD9291 Aniline or a salt thereof wherein the reaction is carried out in the presence of water;
  b) reaction of the resulting AZD9291 Aniline with acryloyl chloride or 3-chloropropanoyl chloride, and where necessary, treatment with base to form AZD9291; and
  c) optional formation of a mesylate salt.

In a further aspect of the present disclosure, there is provided an improved process for the manufacture of AZD9291 or a mesylate salt thereof which comprises:
  a) reaction of AZD9291 Nitrodiamine or a salt thereof with hydrogen, in the presence of a palladium(0)-based catalyst wherein the palladium(0)-based catalyst contains 0.005 molar equivalents of palladium(0), and in the presence of 1.6 molar equivalents of acid wherein the acid comprises methanesulfonic acid, to form AZD9291 Aniline or a salt thereof wherein the reaction is carried out in the presence of a mixture of water and a water-miscible solvent;
  b) reaction of the resulting AZD9291 Aniline with acryloyl chloride or 3-chloropropanoyl chloride, and where necessary, treatment with base to form AZD9291; and
  c) optional formation of a mesylate salt.

In a further aspect of the present disclosure, there is provided an improved process for the manufacture of AZD9291 or a mesylate salt thereof which comprises:
  a) reaction of AZD9291 Nitrodiamine or a salt thereof with hydrogen, in the presence of a palladium(0)-based catalyst wherein the palladium(0)-based catalyst contains 0.005 molar equivalents of palladium(0), and in the presence of 1.6 molar equivalents of acid wherein the acid comprises methanesulfonic acid, to form AZD9291 Aniline or a salt thereof wherein the reaction is carried out in the presence of a mixture of water and a water-miscible solvent wherein the water-miscible solvent is selected from methanol, isopropanol, tetrahydrofuran, acetonitrile, dimethyl sulfoxide and N-methylpyrrolidin-2-one;
  b) reaction of the resulting AZD9291 Aniline with acryloyl chloride or 3-chloropropanoyl chloride, and where necessary, treatment with base to form AZD9291; and
  c) optional formation of a mesylate salt.

In the above aspects it will be understood that the molar equivalents of reactants used are quoted relative to the molar amount of AZD9291 Nitrodiamine used, i.e., 1.0 molar equivalents of AZD9291 Nitrodiamine are assumed to be used by default.

In a further aspect of the present disclosure, there is provided an improved process for the formation of AZD9291 Aniline, or a salt thereof, which comprises:
  a) reaction of AZD9291 Nitrodiamine or a salt thereof with hydrogen, in the presence of a palladium(0)- and/or platinum(0)-based catalyst, and in the presence of an acid, to form AZD9291 Aniline or a salt thereof wherein the reaction is carried out in the presence of water, or in the presence of a mixture of water and a water-miscible solvent; and
  b) optional filtration of the resulting mixture.

In a further aspect of the present disclosure, there is provided an improved process for the formation of AZD9291 Aniline or a salt thereof which comprises:
  a) reaction of AZD9291 Nitrodiamine or a salt thereof with hydrogen, in the presence of a palladium(0)- and/or platinum(0)-based catalyst, and in the presence of an acid wherein the acid comprises an acid selected from a carboxylic acid, a sulfonic acid and a mineral acid, to form AZD9291 Aniline or a salt thereof wherein the reaction is carried out in the presence of water, or in the presence of a mixture of water and a water-miscible solvent; and
  b) optional filtration of the resulting mixture.

In a further aspect of the present disclosure, there is provided an improved process for the formation of AZD9291 Aniline or a salt thereof which comprises:
  a) reaction of AZD9291 Nitrodiamine or a salt thereof with hydrogen, in the presence of a palladium(0)- and/or platinum(0)-based catalyst, and in the presence of an acid wherein the acid comprises an acid selected from ($C_{1-7}$hydrocarbyl)COOH, formic acid, trichloroacetic acid, trifluoroacetic acid, methanesulfonic acid, benzenesulfonic acid, p-toluenesulfonic acid, hydrochloric acid, sulfuric acid and phosphoric acid, to form AZD9291 Aniline or a salt thereof wherein the reaction is carried out in the presence of water, or in the presence of a mixture of water and a water-miscible solvent; and
  b) optional filtration of the resulting mixture.

In a further aspect of the present disclosure, there is provided an improved process for the formation of AZD9291 Aniline or a salt thereof which comprises:
  a) reaction of AZD9291 Nitrodiamine or a salt thereof with hydrogen, in the presence of a palladium(0)- and/or platinum(0)-based catalyst, and in the presence of an acid wherein the acid comprises an acid selected from acetic acid, trifluoroacetic acid, methanesulfonic acid, benzenesulfonic acid, hydrochloric acid, sulfuric acid and phosphoric acid, to form AZD9291 Aniline or a salt thereof wherein the reaction is carried out in the presence of water, or in the presence of a mixture of water and a water-miscible solvent; and
  b) optional filtration of the resulting mixture.

In a further aspect of the present disclosure, there is provided an improved process for the formation of AZD9291 Aniline or a salt thereof which comprises:
  a) reaction of AZD9291 Nitrodiamine or a salt thereof with hydrogen, in the presence of a palladium(0)- and/or platinum(0)-based catalyst, and in the presence of an acid wherein the acid comprises an acid selected from acetic acid, trifluoroacetic acid, methanesulfonic acid, benzenesulfonic acid, hydrochloric acid, sulfuric acid and phosphoric acid, to form AZD9291 Aniline or a salt thereof wherein the reaction is carried out in the presence of water, or in the presence of a mixture of water and a water-miscible solvent; and
  b) optional filtration of the resulting mixture.

In a further aspect of the present disclosure, there is provided an improved process for the formation of AZD9291 Aniline or a salt thereof which comprises:
  a) reaction of AZD9291 Nitrodiamine or a salt thereof with hydrogen, in the presence of a palladium(0)- and/or platinum(0)-based catalyst, and in the presence of at least 1.0 molar equivalents of acid wherein the acid comprises an acid selected from acetic acid, trifluoroacetic acid, methanesulfonic acid, benzenesulfonic acid, hydrochloric acid, sulfuric acid and phosphoric acid, to form AZD9291 Aniline or a salt thereof wherein the reaction is carried out in the presence of water, or in the presence of a mixture of water and a water-miscible solvent; and
  b) optional filtration of the resulting mixture.

In a further aspect of the present disclosure, there is provided an improved process for the formation of AZD9291 Aniline or a salt thereof which comprises:
  a) reaction of AZD9291 Nitrodiamine or a salt thereof with hydrogen, in the presence of a palladium(0)- and/or platinum(0)-based catalyst, and in the presence of at least 1.0 molar equivalents of acid wherein the acid comprises an acid selected from acetic acid, trifluoroacetic acid, methanesulfonic acid, benzenesulfonic acid, hydrochloric acid, sulfuric acid and phosphoric acid, to form AZD9291 Aniline or a salt thereof wherein the reaction is carried out in the presence of water, or in the presence of a mixture of water and a water-miscible solvent wherein the water-miscible solvent is selected from ($C_{1-6}$alkyl)-OH, tetrahydrofuran, acetonitrile, dimethyl sulfoxide, dimethylformamide, dimethylacetamide and N-methylpyrrolidin-2-one; and
  b) optional filtration of the resulting mixture.

In a further aspect of the present disclosure, there is provided an improved process for the formation of AZD9291 Aniline or a salt thereof which comprises:
  a) reaction of AZD9291 Nitrodiamine or a salt thereof with hydrogen, in the presence of a palladium(0)- and/or platinum(0)-based catalyst, and in the presence of 1.0-2.0 molar equivalents of acid wherein the acid comprises an acid selected from acetic acid, trifluoroacetic acid, methanesulfonic acid, benzenesulfonic acid, hydrochloric acid, sulfuric acid and phosphoric acid, to form AZD9291 Aniline or a salt thereof wherein the reaction is carried out in the presence of water, or in the presence of a mixture of water and a water-miscible solvent; and b) optional filtration of the resulting mixture.

In a further aspect of the present disclosure, there is provided an improved process for the formation of AZD9291 Aniline or a salt thereof which comprises:

a) reaction of AZD9291 Nitrodiamine or a salt thereof with hydrogen, in the presence of a palladium(0)- and/or platinum(0)-based catalyst, and in the presence of 1.4-1.6 molar equivalents of acid wherein the acid comprises an acid selected from acetic acid, trifluoroacetic acid, methanesulfonic acid, benzenesulfonic acid, hydrochloric acid, sulfuric acid and phosphoric acid, to form AZD9291 Aniline or a salt thereof wherein the reaction is carried out in the presence of water, or in the presence of a mixture of water and a water-miscible solvent; and b) optional filtration of the resulting mixture.

In a further aspect of the present disclosure, there is provided an improved process for the formation of AZD9291 Aniline or a salt thereof which comprises:

a) reaction of AZD9291 Nitrodiamine or a salt thereof with hydrogen, in the presence of a palladium(0)- and/or platinum(0)-based catalyst, and 1.6 molar equivalents of acid wherein the acid comprises an acid selected from acetic acid, trifluoroacetic acid, methanesulfonic acid, benzenesulfonic acid, hydrochloric acid, sulfuric acid and phosphoric acid, to form AZD9291 Aniline or a salt thereof wherein the reaction is carried out in the presence of water, or in the presence of a mixture of water and a water-miscible solvent; and b) optional filtration of the resulting mixture.

In a further aspect of the present disclosure, there is provided an improved process for the formation of AZD9291 Aniline or a salt thereof which comprises:

a) reaction of AZD9291 Nitrodiamine or a salt thereof with hydrogen, in the presence of a palladium(0)- and/or platinum(0)-based catalyst, and in the presence of 1.5 molar equivalents of acid wherein the acid comprises an acid selected from acetic acid, trifluoroacetic acid, methanesulfonic acid, benzenesulfonic acid, hydrochloric acid, sulfuric acid and phosphoric acid, to form AZD9291 Aniline or a salt thereof wherein the reaction is carried out in the presence of water, or in the presence of a mixture of water and a water-miscible solvent; and b) optional filtration of the resulting mixture.

In a further aspect of the present disclosure, there is provided an improved process for the formation of AZD9291 Aniline or a salt thereof which comprises:

a) reaction of AZD9291 Nitrodiamine or a salt thereof with hydrogen, in the presence of a palladium(0)-based catalyst, and in the presence of 1.5 molar equivalents of acid wherein the acid comprises an acid selected from acetic acid, trifluoroacetic acid, methanesulfonic acid, benzenesulfonic acid, hydrochloric acid, sulfuric acid and phosphoric acid, to form AZD9291 Aniline or a salt thereof wherein the reaction is carried out in the presence of water, or in the presence of a mixture of water and a water-miscible solvent; and b) optional filtration of the resulting mixture.

In a further aspect of the present disclosure, there is provided an improved process for the formation of AZD9291 Aniline or a salt thereof which comprises:

a) reaction of AZD9291 Nitrodiamine or a salt thereof with hydrogen, in the presence of a palladium(0)-based catalyst wherein the palladium(0)-based catalyst contains at least 0.0005 molar equivalents of palladium(0), and in the presence of acid wherein the acid comprises an acid selected from acetic acid, trifluoroacetic acid, methanesulfonic acid, benzenesulfonic acid, hydrochloric acid, sulfuric acid and phosphoric acid, to form AZD9291 Aniline or a salt thereof wherein the reaction is carried out in the presence of water, or in the presence of a mixture of water and a water-miscible solvent; and b) optional filtration of the resulting mixture.

In a further aspect of the present disclosure, there is provided an improved process for the formation of AZD9291 Aniline or a salt thereof which comprises:

a) reaction of AZD9291 Nitrodiamine or a salt thereof with hydrogen, and in the presence of a palladium(0)-based catalyst wherein the palladium(0)-based catalyst contains at least 0.0005 molar equivalents of palladium(0), and in the presence of 1.5 molar equivalents of acid wherein the acid comprises an acid selected from acetic acid, trifluoroacetic acid, methanesulfonic acid, benzenesulfonic acid, hydrochloric acid, sulfuric acid and phosphoric acid, to form AZD9291 Aniline or a salt thereof wherein the reaction is carried out in the presence of water, or in the presence of a mixture of water and a water-miscible solvent; and b) optional filtration of the resulting mixture.

In a further aspect of the present disclosure, there is provided an improved process for the formation of AZD9291 Aniline or a salt thereof which comprises:

a) reaction of AZD9291 Nitrodiamine or a salt thereof with hydrogen, and in the presence of a palladium(0)-based catalyst wherein the palladium(0)-based catalyst contains at least 0.005 molar equivalents of palladium(0), and in the presence of 1.5 molar equivalents of acid wherein the acid comprises an acid selected from acetic acid, trifluoroacetic acid, methanesulfonic acid, benzenesulfonic acid, hydrochloric acid, sulfuric acid and phosphoric acid, to form AZD9291 Aniline or a salt thereof wherein the reaction is carried out in the presence of water, or in the presence of a mixture of water and a water-miscible solvent; and b) optional filtration of the resulting mixture.

In a further aspect of the present disclosure, there is provided an improved process for the formation of AZD9291 Aniline or a salt thereof which comprises:

a) reaction of AZD9291 Nitrodiamine or a salt thereof with hydrogen, in the presence of a palladium(0)-based catalyst wherein the palladium(0)-based catalyst contains 0.005 molar equivalents of palladium(0), and in the presence of 1.5 molar equivalents of acid wherein the acid comprises an acid selected from acetic acid, trifluoroacetic acid, methanesulfonic acid, benzenesulfonic acid, hydrochloric acid, sulfuric acid and phosphoric acid, to form AZD9291 Aniline or a salt thereof wherein the reaction is carried out in the presence of water, or in the presence of a mixture of water and a water-miscible solvent; and b) optional filtration of the resulting mixture.

In a further aspect of the present disclosure, there is provided an improved process for the formation of AZD9291 Aniline or a salt thereof which comprises:

a) reaction of AZD9291 Nitrodiamine or a salt thereof with hydrogen, and in the presence of a platinum(0)-based catalyst, and in the presence of 1.5 molar equivalents of acid wherein the acid comprises an acid selected from acetic acid, trifluoroacetic acid, methanesulfonic acid, benzenesulfonic acid, hydrochloric acid, sulfuric acid and phosphoric acid, to form AZD9291 Aniline or a salt thereof wherein the reaction is carried out in the presence of water, or in the presence of a mixture of water and a water-miscible solvent; and b) optional filtration of the resulting mixture.

In a further aspect of the present disclosure, there is provided an improved process for the formation of AZD9291 Aniline or a salt thereof which comprises:

a) reaction of AZD9291 Nitrodiamine or a salt thereof with hydrogen, in the presence of a platinum(0)-based catalyst wherein the platinum(0)-based catalyst contains at least 0.0001 molar equivalents of platinum(0), and in the presence of 1.5 molar equivalents of acid wherein the acid comprises an acid selected from acetic acid, trifluoroacetic acid, methanesulfonic acid, benzenesulfonic acid, hydrochloric acid, sulfuric acid or phosphoric acid, to form AZD9291 Aniline or a salt thereof wherein the reaction is carried out in the presence of water, or in the presence of a mixture of water and a water-miscible solvent; and b) optional filtration of the resulting mixture.

In a further aspect of the present disclosure, there is provided an improved process for the formation of AZD9291 Aniline or a salt thereof which comprises:

a) reaction of AZD9291 Nitrodiamine or a salt thereof with hydrogen, in the presence of a platinum(0)-based catalyst wherein the platinum(0)-based catalyst contains at least 0.001 molar equivalents of platinum(0), and in the presence of 1.5 molar equivalents of acid wherein the acid comprises an acid selected from acetic acid, trifluoroacetic acid, methanesulfonic acid, benzenesulfonic acid, hydrochloric acid, sulfuric acid or phosphoric acid, to form AZD9291 Aniline or a salt thereof wherein the reaction is carried out in the presence of water, or in the presence of a mixture of water and a water-miscible solvent; and b) optional filtration of the resulting mixture.

In a further aspect of the present disclosure, there is provided an improved process for the formation of AZD9291 Aniline or a salt thereof which comprises:

a) reaction of AZD9291 Nitrodiamine or a salt thereof with hydrogen, in the presence of a platinum(0)-based catalyst wherein the platinum(0)-based catalyst contains 0.001 molar equivalents of platinum(0), and in the presence of an acid wherein the acid comprises an acid selected from acetic acid, trifluoroacetic acid, methanesulfonic acid, benzenesulfonic acid, hydrochloric acid, sulfuric acid and phosphoric acid, to form AZD9291 Aniline or a salt thereof wherein the reaction is carried out in the presence of water, or in the presence of a mixture of water and a water-miscible solvent; and b) optional filtration of the resulting mixture.

In a further aspect of the present disclosure, there is provided an improved process for the formation of AZD9291 Aniline or a salt thereof which comprises:

a) reaction of AZD9291 Nitrodiamine or a salt thereof with hydrogen in the presence of a platinum(0)-based catalyst wherein the platinum(0)-based catalyst contains 0.001 molar equivalents of platinum(0), and in the presence of 1.5 molar equivalents of acid wherein the acid comprises an acid selected from acetic acid, trifluoroacetic acid, methanesulfonic acid, benzenesulfonic acid, hydrochloric acid, sulfuric acid and phosphoric acid, to form AZD9291 Aniline or a salt thereof wherein the reaction is carried out in the presence of water, or in the presence of a mixture of water and a water-miscible solvent; and b) optional filtration of the resulting mixture.

In a further aspect of the present disclosure, there is provided an improved process for the formation of AZD9291 Aniline or a salt thereof which comprises:

a) reaction of AZD9291 Nitrodiamine or a salt thereof with hydrogen, in the presence of a palladium(0)- and/or platinum(0)-based catalyst wherein the palladium(0)-based catalyst (if present) contains 0.005 molar equivalents of palladium(0) and the platinum(0)-based catalyst (if present) contains 0.001 molar equivalents of platinum(0), and in the presence of at least 1.0 molar equivalents of acid wherein the acid comprises an acid selected from acetic acid, trifluoroacetic acid, methanesulfonic acid, benzenesulfonic acid, hydrochloric acid, sulfuric acid and phosphoric acid, to form AZD9291 Aniline or a salt thereof wherein the reaction is carried out in the presence of water; and b) optional filtration of the resulting mixture.

In a further aspect of the present disclosure, there is provided an improved process for the formation of AZD9291 Aniline or a salt thereof which comprises:

a) reaction of AZD9291 Nitrodiamine or a salt thereof with hydrogen, in the presence of a palladium(0)- and/or platinum(0)-based catalyst wherein the palladium(0)-based catalyst (if present) contains 0.005 molar equivalents of palladium(0) and the platinum(0)-based catalyst (if present) contains 0.001 molar equivalents of platinum(0), and in the presence of at least 1.4-1.6 molar equivalents of acid wherein the acid comprises an acid selected from acetic acid, trifluoroacetic acid, methanesulfonic acid, benzenesulfonic acid, hydrochloric acid, sulfuric acid and phosphoric acid, to form AZD9291 Aniline or a salt thereof wherein the reaction is carried out in the presence of water; and b) optional filtration of the resulting mixture.

In a further aspect of the present disclosure, there is provided an improved process for the formation of AZD9291 Aniline or a salt thereof which comprises:

a) reaction of AZD9291 Nitrodiamine or a salt thereof with hydrogen, in the presence of a palladium(0)- and/or platinum(0)-based catalyst wherein the palladium(0)-based catalyst (if present) contains 0.005 molar equivalents of palladium(0) and the platinum(0)-based catalyst (if present) contains 0.001 molar equivalents of platinum(0), and in the presence of 1.5 molar equivalents of acid wherein the acid comprises an acid selected from acetic acid, trifluoroacetic acid, methanesulfonic acid, benzenesulfonic acid, hydrochloric acid, sulfuric acid and phosphoric acid, to form AZD9291 Aniline or a salt thereof wherein the reaction is carried out in the presence of water; and b) optional filtration of the resulting mixture.

In a further aspect of the present disclosure, there is provided an improved process for the formation of AZD9291 Aniline or a salt thereof which comprises:

a) reaction of AZD9291 Nitrodiamine or a salt thereof with hydrogen, in the presence of a palladium(0)- and/or platinum(0)-based catalyst wherein the palladium(0)-based catalyst (if present) contains 0.005 molar equivalents of palladium(0) and the platinum(0)-based catalyst (if present) contains 0.001 molar equivalents of platinum(0), and in the presence of 1.6 molar equivalents of acid wherein the acid comprises an acid selected from acetic acid, trifluoroacetic acid, methanesulfonic acid, benzenesulfonic acid, hydrochloric acid, sulfuric acid and phosphoric acid, to form AZD9291 Aniline or a salt thereof wherein the reaction is carried out in the presence of water; and b) optional filtration of the resulting mixture.

In a further aspect of the present disclosure, there is provided an improved process for the formation of AZD9291 Aniline or a salt thereof which comprises:

a) reaction of AZD9291 Nitrodiamine or a salt thereof with hydrogen, in the presence of a palladium(0)- and/or platinum(0)-based catalyst wherein the palladium(0)-based catalyst (if present) contains 0.005 molar equivalents of palladium(0) and the platinum(0)-based catalyst (if present) contains 0.001 molar equivalents of platinum(0), and in the presence of at least 1.0 molar equivalents of an acid wherein the acid comprises methanesulfonic acid, to form AZD9291 Aniline or a salt thereof wherein the reaction is carried out in the presence of water; and b) optional filtration of the resulting mixture.

In a further aspect of the present disclosure, there is provided an improved process for the formation of AZD9291 Aniline which comprises:

a) reaction of AZD9291 Nitrodiamine or a salt thereof with hydrogen, in the presence of a palladium(0)- and/or platinum(0)-based catalyst wherein the palladium(0)-based catalyst (if present) contains 0.005 molar equivalents of palladium(0) and the platinum(0)-based catalyst (if present) contains 0.001 molar equivalents of platinum(0), and in the presence of at least 1.4-1.6 molar equivalents of an acid wherein the acid comprises methanesulfonic acid, to form AZD9291 Aniline or a salt thereof wherein the reaction is carried out in the presence of water; and b) optional filtration of the resulting mixture.

In a further aspect of the present disclosure, there is provided an improved process for the formation of AZD9291 Aniline or a salt thereof which comprises:

a) reaction of AZD9291 Nitrodiamine or a salt thereof with hydrogen, in the presence of a palladium(0)- and/or platinum(0)-based catalyst wherein the palladium(0)-based catalyst (if present) contains 0.005 molar equivalents of palladium(0) and the platinum(0)-based catalyst (if present) contains 0.001 molar equivalents of platinum(0), and in the presence of 1.5 molar equivalents of acid wherein the acid comprises an acid selected from acetic acid, trifluoroacetic acid, methanesulfonic acid, benzenesulfonic acid, hydrochloric acid, sulfuric acid and phosphoric acid, to form AZD9291 Aniline or a salt thereof wherein the reaction is carried out in the presence of water; and b) optional filtration of the resulting mixture.

In a further aspect of the present disclosure, there is provided an improved process for the formation of AZD9291 Aniline or a salt thereof which comprises:

a) reaction of AZD9291 Nitrodiamine or a salt thereof with hydrogen, in the presence of a palladium(0)- and/or platinum(0)-based catalyst wherein the palladium(0)-based catalyst (if present) contains 0.005 molar equivalents of palladium(0) and the platinum(0)-based catalyst (if present) contains 0.001 molar equivalents of platinum(0), and in the presence of 1.6 molar equivalents of acid wherein the acid comprises an acid selected from acetic acid, trifluoroacetic acid, methanesulfonic acid, benzenesulfonic acid, hydrochloric acid, sulfuric acid and phosphoric acid, to form AZD9291 Aniline or a salt thereof wherein the reaction is carried out in the presence of water; and b) optional filtration of the resulting mixture.

In a further aspect of the present disclosure, there is provided an improved process for the formation of AZD9291 Aniline or a salt thereof which comprises:

a) reaction of AZD9291 Nitrodiamine or a salt thereof with hydrogen, in the presence of a palladium(0)-based catalyst or a platinum(0)-based catalyst, and in the presence of an acid wherein the acid comprises an acid selected from acetic acid, trifluoroacetic acid, methanesulfonic acid, benzenesulfonic acid, hydrochloric acid, sulfuric acid and phosphoric acid, to form AZD9291 Aniline or a salt thereof wherein the reaction is carried out in the presence a mixture of water and a water-miscible solvent; and b) optional filtration of the resulting mixture.

In a further aspect of the present disclosure, there is provided an improved process for the formation of AZD9291 Aniline or a salt thereof which comprises:

a) reaction of AZD9291 Nitrodiamine or a salt thereof with hydrogen, in the presence of a palladium(0)- and/or platinum(0)-based catalyst wherein the palladium(0)-based catalyst (if present) contains 0.005 molar equivalents of palladium(0) and the platinum(0)-based catalyst (if present) contains 0.001 molar equivalents of platinum(0), and in the presence of 1.5 molar equivalents of acid wherein the acid comprises an acid selected from acetic acid, trifluoroacetic acid, methanesulfonic acid, benzenesulfonic acid, hydrochloric acid, sulfuric acid and phosphoric acid, to form AZD9291 Aniline or a salt thereof wherein the reaction is carried out in the presence of a mixture of water and a water-miscible solvent; and b) optional filtration of the resulting mixture.

In a further aspect of the present disclosure, there is provided an improved process for the formation of AZD9291 Aniline or a salt thereof which comprises:

a) reaction of AZD9291 Nitrodiamine or a salt thereof with hydrogen, in the presence of a palladium(0)- and/or platinum(0)-based catalyst wherein the palladium(0)-based catalyst (if present) contains 0.005 molar equivalents of palladium(0) and the platinum(0)-based catalyst (if present) contains 0.001 molar equivalents of platinum(0), and in the presence of 1.5 molar equivalents of acid wherein the acid comprises an acid selected from acetic acid, trifluoroacetic acid, methanesulfonic acid, benzenesulfonic acid, hydrochloric acid, sulfuric acid and phosphoric acid, to form AZD9291 Aniline or a salt thereof, wherein the reaction is carried out in the presence of a mixture of water and a water-miscible solvent selected from an alcohol, tetrahydrofuran, acetonitrile, dimethyl sulfoxide and N-methylpyrrolidin-2-one; and b) optional filtration of the resulting mixture.

In a further aspect of the present disclosure, there is provided an improved process for the formation of AZD9291 Aniline or a salt thereof which comprises:

a) reaction of AZD9291 Nitrodiamine or a salt thereof with hydrogen, in the presence of a palladium(0)- and/or platinum(0)-based catalyst wherein the palladium(0)-based catalyst (if present) contains 0.005 molar equivalents of palladium(0) and the platinum(0)-based catalyst (if present) contains 0.001 molar equivalents of platinum(0), and in the presence of 1.5 molar equivalents of acid wherein the acid comprises an acid selected from acetic acid, trifluoroacetic acid, methanesulfonic acid, benzenesulfonic acid, hydrochloric acid, sulfuric acid and phosphoric acid, to form AZD9291 Aniline or a salt thereof, wherein the reaction is carried out in the presence of a mixture of water and a water-miscible solvent selected from $(C_{1-6}alkyl)$-OH, tetrahydrofuran, acetonitrile, dimethyl sulfoxide, dimethylformamide, dimethylacetamide and N-methylpyrrolidin-2-one; and b) optional filtration of the resulting mixture.

In a further aspect of the present disclosure, there is provided an improved process for the formation of AZD9291 Aniline or a salt thereof which comprises:

a) reaction of AZD9291 Nitrodiamine or a salt thereof with hydrogen, in the presence of a palladium(0)- and/or platinum(0)-based catalyst wherein the palladium(0)-based catalyst (if present) contains 0.005 molar equivalents of palladium(0) and the platinum(0)-based catalyst (if present) contains 0.001 molar equivalents of platinum(0), and in the presence of 1.5 molar equivalents of acid wherein the acid comprises an acid selected from acetic acid, trifluoroacetic acid, methanesulfonic acid, benzenesulfonic acid, hydrochloric acid, sulfuric acid and phosphoric acid, to form AZD9291 Aniline or a salt thereof, wherein the reaction is carried out in the presence of a mixture of water and a water-miscible solvent selected from methanol, ethanol, propanol, tetrahydrofuran, acetonitrile, dimethyl sulfoxide, dimethylformamide, dimethylacetamide and N-methylpyrrolidin-2-one; and b) optional filtration of the resulting mixture.

In a further aspect of the present disclosure, there is provided an improved process for the formation of AZD9291 Aniline or a salt thereof which comprises:

a) reaction of AZD9291 Nitrodiamine or a salt thereof with hydrogen, in the presence of a palladium(0)- and/or platinum(0)-based catalyst wherein the palladium(0)-based catalyst (if present) contains 0.005 molar equivalents of palladium(0) and the platinum(0)-based catalyst (if present) contains 0.001 molar equivalents of platinum(0), and in the presence of 1.5 molar equivalents of acid wherein the acid comprises an acid selected from acetic acid, trifluoroacetic acid, methanesulfonic acid, benzenesulfonic acid, hydrochloric acid, sulfuric acid and phosphoric acid, to form AZD9291 Aniline or a salt thereof, wherein the reaction is carried out in the presence of a mixture of water and a water-miscible solvent selected from methanol, ethanol, n-propanol, isopropanol, tetrahydrofuran, acetonitrile, dimethyl sulfoxide, dimethylformamide, dimethylacetamide and N-methylpyrrolidin-2-one; and b) optional filtration of the resulting mixture.

In a further aspect of the present disclosure, there is provided an improved process for the formation of AZD9291 Aniline or a salt thereof which comprises:

a) reaction of AZD9291 Nitrodiamine or a salt thereof with hydrogen, in the presence of a palladium(0)- and/or platinum(0)-based catalyst wherein the palladium(0)-based catalyst (if present) contains 0.005 molar equivalents of palladium(0) and the platinum(0)-based catalyst (if present) contains 0.001 molar equivalents of platinum(0), and in the presence of at least 1.0 molar equivalents of acid wherein the acid comprises an acid selected from acetic acid, trifluoroacetic acid, methanesulfonic acid, benzenesulfonic acid, hydrochloric acid, sulfuric acid and phosphoric acid, to form AZD9291 Aniline or a salt thereof wherein the reaction is carried out in the presence of a mixture of water and a water-miscible solvent selected from methanol, isopropanol, tetrahydrofuran, acetonitrile, dimethyl sulfoxide and N-methylpyrrolidin-2-one; and b) optional filtration of the resulting mixture.

In a further aspect of the present disclosure, there is provided an improved process for the formation of AZD9291 Aniline or a salt thereof which comprises:

a) reaction of AZD9291 Nitrodiamine or a salt thereof with hydrogen, in the presence of a palladium(0)- and/or platinum(0)-based catalyst wherein the palladium(0)-based catalyst (if present) contains 0.005 molar equivalents of palladium(0) and the platinum(0)-based catalyst (if present) contains 0.001 molar equivalents of platinum(0), and in the presence of 1.5 molar equivalents of acid wherein the acid comprises an acid selected from acetic acid, trifluoroacetic acid, methanesulfonic acid, benzenesulfonic acid, hydrochloric acid, sulfuric acid and phosphoric acid, to form AZD9291 Aniline or a salt thereof wherein the reaction is carried out in the presence of a mixture of water and a water-miscible solvent selected from methanol, isopropanol, tetrahydrofuran, acetonitrile, dimethyl sulfoxide and N-methylpyrrolidin-2-one; and b) optional filtration of the resulting mixture.

In a further aspect of the present disclosure, there is provided an improved process for the formation of AZD9291 Aniline or a salt thereof which comprises:

a) reaction of AZD9291 Nitrodiamine or a salt thereof with hydrogen, in the presence of a palladium(0)- and/or platinum(0)-based catalyst wherein the palladium(0)-based catalyst (if present) contains 0.005 molar equivalents of palladium(0) and the platinum(0)-based catalyst (if present) contains 0.001 molar equivalents of platinum(0), and in the presence of 1.6 molar equivalents of acid wherein the acid comprises an acid selected from acetic acid, trifluoroacetic acid, methanesulfonic acid, benzenesulfonic acid, hydrochloric acid, sulfuric acid and phosphoric acid, to form AZD9291 Aniline or a salt thereof wherein the reaction is carried out in the presence of a mixture of water and a water-miscible solvent selected from methanol, isopropanol, tetrahydrofuran, acetonitrile, dimethyl sulfoxide and N-methylpyrrolidin-2-one; and b) optional filtration of the resulting mixture.

In a further aspect of the present disclosure, there is provided an improved process for the formation of AZD9291 Aniline or a salt thereof which comprises:

a) reaction of AZD9291 Nitrodiamine or a salt thereof with hydrogen, in the presence of a palladium(0)- and/or platinum(0)-based catalyst wherein the palladium(0)-based catalyst (if present) contains 0.005 molar equivalents of palladium(0) and the platinum(0)-based catalyst (if present) contains 0.001 molar equivalents of platinum(0), and in the presence of 1.4-1.6 molar equivalents of acid wherein the acid comprises an acid selected from acetic acid, trifluoroacetic acid, methanesulfonic acid, benzenesulfonic acid, hydrochloric acid, sulfuric acid and phosphoric acid, to form AZD9291 Aniline or a salt thereof wherein the reaction is carried out in the presence of a mixture of water and a water-miscible solvent selected from methanol, isopropanol, tetrahydrofuran, acetonitrile, dimethyl sulfoxide and N-methylpyrrolidin-2-one; and b) optional filtration of the resulting mixture.

In a further aspect of the present disclosure, there is provided an improved process for the formation of AZD9291 Aniline or a salt thereof which comprises:

a) reaction of AZD9291 Nitrodiamine or a salt thereof with hydrogen, in the presence of a palladium(0)- and/or platinum(0)-based catalyst wherein the palladium(0)-based catalyst (if present) contains 0.005 molar equivalents of palladium(0) and the platinum(0)-based catalyst (if present) contains 0.001 molar equivalents of platinum(0), and in the presence of at least 1.0 molar equivalents of an acid wherein the acid comprises methanesulfonic acid, to form AZD9291 Aniline or a salt thereof wherein the reaction is carried out in the presence of a mixture of water and a water-miscible solvent selected from methanol, isopropanol, tetrahydrofuran, acetonitrile, dimethyl sulfoxide and N-methylpyrrolidin-2-one; and b) optional filtration of the resulting mixture.

In a further aspect of the present disclosure, there is provided an improved process for the formation of AZD9291 Aniline or a salt thereof which comprises:

a) reaction of AZD9291 Nitrodiamine or a salt thereof with hydrogen, in the presence of a palladium(0)- and/or platinum(0)-based catalyst wherein the palladium(0)-based catalyst (if present) contains 0.005 molar equivalents of palladium(0) and the platinum(0)-based catalyst (if present) contains 0.001 molar equivalents of platinum(0), and in the presence of 1.5 molar equivalents of an acid wherein the acid comprises methanesulfonic acid, to form AZD9291 Aniline or a salt thereof wherein the reaction is carried out in the presence of a mixture of water and a water-miscible solvent selected from methanol, isopropanol, tetrahydrofuran, acetonitrile, dimethyl sulfoxide or N-methylpyrrolidin-2-one; and b) optional filtration of the resulting mixture.

In a further aspect of the present disclosure, there is provided an improved process for the formation of AZD9291 Aniline or a salt thereof which comprises:

a) reaction of AZD9291 Nitrodiamine or a salt thereof with hydrogen, in the presence of a palladium(0)- and/or platinum(0)-based catalyst wherein the palladium(0)-based catalyst (if present) contains 0.005 molar equivalents of palladium(0) and the platinum(0)-based catalyst (if present) contains 0.001 molar equivalents of platinum(0), and in the presence of 1.6 molar equivalents of an acid wherein the acid comprises methanesulfonic acid, to form AZD9291 Aniline or a salt thereof wherein the reaction is carried out in the presence of a mixture of water and a water-miscible solvent selected from methanol, isopropanol, tetrahydrofuran, acetonitrile, dimethyl sulfoxide and N-methylpyrrolidin-2-one; and b) optional filtration of the resulting mixture.

In a further aspect of the present disclosure, there is provided an improved process for the formation of AZD9291 Aniline or a salt thereof which comprises:

a) reaction of AZD9291 Nitrodiamine or a salt thereof with hydrogen, in the presence of a palladium(0)- and/or platinum(0)-based catalyst wherein the palladium(0)-based catalyst (if present) contains 0.005 molar equivalents of palladium(0) and the platinum(0)-based catalyst (if present) contains 0.001 molar equivalents of platinum(0), and in the presence of 1.4-1.6 molar equivalents of an acid wherein the acid comprises methanesulfonic acid, to form AZD9291 Aniline or a salt thereof wherein the reaction is carried out in the presence of a mixture of water and a water-miscible solvent selected from methanol, isopropanol, tetrahydrofuran, acetonitrile, dimethyl sulfoxide and N-methylpyrrolidin-2-one; and b) optional filtration of the resulting mixture.

In the above aspects it will be understood that the molar equivalents of reactants used are quoted relative to the amount of AZD9291 Nitrodiamine used, i.e., 1.0 molar equivalents of AZD9291 Nitrodiamine are assumed to be used by default.

A further aspect of the present disclosure provides the compound AZD9291 or a pharmaceutically acceptable salt thereof made by the process steps a) to c) as hereinbefore described.

A further aspect of the present disclosure provides the compound AZD9291 Aniline or a salt thereof made by the process step a) as described in any aspects, or embodiments or claims disclosed herein.

Another aspect of the present disclosure provides a process for the preparation of AZD9291 Aniline or a salt thereof which comprises step a) of the process described in any aspects, embodiments or claims disclosed herein.

A further aspect of the present disclosure provide a pharmaceutical composition comprising the compound AZD9291 or a pharmaceutically acceptable salt thereof made by the process steps a) to c) as described in any aspects, embodiments or claims disclosed herein.

Another aspect of the present disclosure provide a pharmaceutical composition comprising the compound AZD9291 or a pharmaceutically acceptable salt thereof made by the process steps a) to c) as described in any aspects, embodiments or claims disclosed herein in association with one or more pharmaceutically acceptable diluents, carriers or excipients.

Therefore a further aspect of the present disclosure provides a product obtainable by the process described by any aspects, embodiments or claims of the present disclosure.

Another aspect of the present disclosure provides a product obtained by the process described by any aspects, embodiments or claims of the present disclosure.

One or more aspects, embodiments and claims disclosed herein may be combined together to provide further aspects, embodiments and claims, in all combinations, except where the context means a given combination would clearly not be appropriate/not make sense.

Abbreviations

Barg pressure, in units of bars, above atmospheric pressure

Psig pounds per square inch gauge

The present disclosure is further illustrated by the following examples.

EXAMPLE 1

AZD9291 Nitrodiamine (10.0 g), 5% platinum-on-activated carbon (0.001 molar equivalents, 50% water wet, 0.2 g, 0.02 relative weight), methanesulfonic acid (3.23 g, 1.6 molar equivalents) and water (100 mL, 10 relative volume) were mixed in a sealed autoclave. The headspace was inerted by 5 cycles of nitrogen pressurisation. The mixture was warmed to 50° C., and the headspace was purged by 3 cycles of pressurisation with hydrogen. The mixture was stirred for 4 hours at 50° C., dosing hydrogen gas to maintain a headspace pressure of 2 barg. The vessel was inerted by nitrogen purge cycles, and the mixture was filtered to remove catalyst particles. The clear filtrates were mixed with 2-methyltetrahydrofuran (60 mL, 6 relative volumes) and 2 M sodium hydroxide solution in water (19 mL, 1.8 mol eq). After a period of mixing, the mixture was settled and the lower aqueous layer was discarded. The organic layer was washed once with water (80 mL, 8 relative volumes) and then diluted with 2-methyltetrahydrofuran (80 mL, 8 relative volumes). The product solution in 2-methyltetrahydrofuran was distilled at 50° C. under reduced pressure, to a residual volume of 60 mL. AZD9291 Aniline (seed) was added, and the mixture was cooled to 0° C. over 4 hours. The resulting slurry was filtered, and the solids collected were washed with 2-methyltetrahydrofuran (20 mL, 2 relative volumes) to yield AZD9291 Aniline as an off-white powder (7.0 g, 75% yield) after drying under vacuum. No detectable levels of AZD9291 Aniline Hydroxy were detected in the resulting AZD9291 Aniline by UPLC.

UPLC Methodology

| Apparatus: | An ultra performance liquid chromatograph fitted with a UV detector. The system should be capable of delivering a linear gradient. |
|---|---|
| Column: | UPLC BEH Phenyl 1.7 um, 2.1 × 100 mm, or equivalent |
| Phase A: | 0.06% v/v trifluoroacetic acid in water |
| Phase B: | 0.06% v/v trifluoroacetic acid in acetonitrile |

| Gradient profile[1]: | Time (minutes) | Phase A | Phase B |
|---|---|---|---|
| | 0.0 | 90 | 10 |
| | 13 | 85 | 15 |
| | 20 | 30 | 70 |
| | 22 | 90 | 10 |

| Flow rate: | 0.6 mL min$^{-1}$ |
|---|---|
| Injection volume: | 1 μL |
| Column temperature: | 45° C. |
| Sample temperature: | 5° C. |
| Wavelength: | 245 nm |
| Sample concentration: | 1.0 mg/mL (approximately) |
| Diluent: | 40/60/0.1 v/v MeCN/water/trifluoroacetic acid |

EXAMPLE 2

Illustrated below is a general synthesis of AZD9291 Aniline wherein the aqueous acid, catalyst and solvent system were varied. Table 1 details the identities of these variables and the quantities used where applicable. Table 2 provides results from the HPLC analysis of AZD9291 Aniline synthesised according to the methodology detailed below.

General Synthesis of AZD9291 Aniline

To a Biotage Endeavor glass liner, AZD9291 Nitrodiamine (290 to 310 mg), catalyst (variable type, variable amounts), solvent (10 relative volumes, 3.0 mL) and acid (variable type, 1.5 molar equivalents). The liner was placed in the Endeavor hydrogenation block, and the block was sealed. The manifold was purged with nitrogen. The vessel was purged with nitrogen purge three times (to 4 barg, no agitation). The manifold was purged with hydrogen. The program was started, with instruction to:

heat to 50° C.
Agitate at 300 rpm for 10 minutes.
Charge hydrogen to a total headspace pressure of 44 psig, giving a total hydrogen partial pressure of 44 psi.
Agitate at 1000 rpm, maintain hydrogen pressure, monitor uptake.

The reaction was stopped after between 3 and 4 hours under hydrogen. The block was opened to atmosphere. The reaction mixture was filtered through a 0.45-μm hydrophilic syringe filter (Millipore LHM), to remove catalyst residues. The filtrate was sampled for HPLC analysis (1 drop in 1.5 mL of 75:25:0.1 (v/v/v) MeCN/Water/trifluoroacetic acid).

HPLC Methodology

| Apparatus: | A liquid chromatograph fitted with a UV detector. The system should be capable of delivering a linear gradient. |
|---|---|
| Column: | 30 × 4.6 mm XBridge BEH C18 1.7 μm (Waters), or equivalent |

| Gradient profile[1]: | Time (minutes) | Water ratio | Acetonitrile ratio | Ammonium acetate (% w/v) |
|---|---|---|---|---|
| | 0.0 | 95 | 5 | 0.01 |
| | 5.2 | 10 | 90 | 0.01 |
| | 5.7 | 10 | 90 | 0.01 |
| | 5.8 | 95 | 5 | 0.01 |

| Data collection time: | 6.2 mins |
|---|---|
| Overall run time: | 8.5 mins including equilibration |
| Flow rate: | 2.0 mL min$^{-1}$ |
| Injection volume: | 5 μL |
| Column temperature: | 40° C. |
| Wavelength: | 225 nm |

TABLE 1

Identities of acid, solvent and catalyst used, and quantities of acid and catalyst used in the synthesis of AZD9291 Aniline as illustrated in example 2.

| Experiment | Acid | Solvent | Catalyst-metal type | Catalyst (Manufacturer details) | Quantity of catalyst added (molar equivalents) [1, 2] | Time to end of uptake (hours) |
|---|---|---|---|---|---|---|
| A | Methanesulfonic acid | Water | Platinum/Vanadium | CF1082 BV/W (1% Pt + 2% V/C) (Evonik) | 0.001[3] | 1.5 |
| B | Methanesulfonic acid | Water | Platinum | Type 18 (5% Pt/C) (Johnson Matthey) | 0.001 | 1.4 |
| C | Methanesulfonic acid | Water | Palladium | Type 490 (10% Pd/C) (Johnson Matthey) | 0.005 | 3.3 |

TABLE 1-continued

Identities of acid, solvent and catalyst used, and quantities of acid and catalyst used in the synthesis of AZD9291 Aniline as illustrated in example 2.

| Experiment | Acid | Solvent | Catalyst-metal type | Catalyst (Manufacturer details) | Quantity of catalyst added (molar equivalents) [1, 2] | Time to end of uptake (hours) |
|---|---|---|---|---|---|---|
| D | Methanesulfonic acid | Water | Ruthenium | Type 97 (5% Ru/C) (Johnson Matthey) | 0.005 | No reaction or very slow reaction |
| E | Methanesulfonic acid | Water | Rhodium | Type 592 (5% Rh/C) (Johnson Matthey) | 0.005 | 1.3 |
| F | Methanesulfonic acid | 80:20 v/v Methanol/water | Platinum | Type 18 (5% Pt/C) (Johnson Matthey) | 0.001 | 0.7 |
| G | Methanesulfonic acid | 80:20 v/v Isopropanol/water | Platinum | Type 18 (5% Pt/C) (Johnson Matthey) | 0.001 | 0.4 |
| H | Methanesulfonic acid | 80:20 v/v Tetrahydrofuran/water | Platinum | Type 18 (5% Pt/C) (Johnson Matthey) | 0.001 | 1.0 |
| J | Methanesulfonic acid | 80:20 v/v Acetone/water | Platinum | Type 18 (5% Pt/C) (Johnson Matthey) | 0.001 | 1.0 |
| K | Methanesulfonic acid | 80:20 v/v Acetonitrile/water | Platinum | Type 18 (5% Pt/C) (Johnson Matthey) | 0.001 | 1.1 |
| L[5] | Methanesulfonic acid | 80:20 v/v Dimethyl sulfoxide/water | Platinum | Type 18 (5% Pt/C) (Johnson Matthey) | 0.001 | >4 |
| M | Methanesulfonic acid | 80:20 v/v N-Methylpyrrolidinone/water | Platinum | Type 18 (5% Pt/C) (Johnson Matthey) | 0.001 | 2.0 |
| N | Acetic acid | Water | Platinum | Type 18 (5% Pt/C) (Johnson Matthey) | 0.001 | 1.3 |
| P | Trifluoroacetic acid | Water | Platinum | Type 18 (5% Pt/C) (Johnson Matthey) | 0.001 | 1.0 |
| Q | Benzenesulfonic acid | Water | Platinum | Type 18 (5% Pt/C) (Johnson Matthey) | 0.001 | 2.0 |
| R | hydrochloric acid | Water | Platinum | Type 18 (5% Pt/C) (Johnson Matthey) | 0.001 | 2.6 |
| S | Sulfuric acid[4] | Water | Platinum | Type 18 (5% Pt/C) (Johnson Matthey) | 0.001 | 1.6 |
| T | Phosphoric acid | Water | Platinum | Type 18 (5% Pt/C) (Johnson Matthey) | 0.001 | 1.8 |
| U[5] | Methanesulfonic acid | 80:20 v/v Dimethyl sulfoxide/water | Platinum | Type 18 (5% Pt/C) (Johnson Matthey) | 0.0025 | Not recorded |
| V | Trifluoroacetic acid | 80:20 v/v Tetrahydrofuran/water | Platinum | Type 18 (5% Pt/C) (Johnson Matthey) | 0.0005 | See footnote [6] |

TABLE 1-continued

Identities of acid, solvent and catalyst used, and quantities of acid and catalyst used in the synthesis of AZD9291 Aniline as illustrated in example 2.

| Experiment | Acid | Solvent | Catalyst-metal type | Catalyst (Manufacturer details) | Quantity of catalyst added (molar equivalents) [1, 2] | Time to end of uptake (hours) |
|---|---|---|---|---|---|---|
| W | Sulfuric acid[4] | 80:20 v/v N-Methylpyrrolidinone/water | Palladium | Type 490 (10% Pd/C) (Johnson Matthey) | 0.01 | Not recorded |
| X | Acetic acid | 80:20 v/v Acetonitrile/water | Palladium | Type 490 (10% Pd/C) (Johnson Matthey) | 0.005 | Not recorded |

[1] Relative to AZD9291 Nitrodiamine
[2] Quantity of catalyst added refers to amount of precious metal added to reaction mixture rather than amount of catalyst.
[3] Catalyst charge relative to amount of platinum in the catalyst.
[4] For reactions using sulfuric acid, the charge was 0.75 mol eq, since sulfuric acid is diprotic and the second pKa (2) is acidic enough to have the same effect as the first.
[5] Reaction L was repeated (see reaction U) with a higher catalyst loading (0.0025 mol eq, vs 0.001 mol eq), in order to obtain complete conversion.
[6] This experiment was much slower than expected, so after reaction N, P, Q, R, S and T, which were run simultaneously to reaction V, were complete and sampled for HPLC analysis, more catalyst (16 mg, 0.003 mol eq) was added to reaction V, and the reaction was re-started. A sample from reaction V was taken after a further 60 minutes under the same conditions, after which the reaction was complete.

TABLE 2

HPLC analysis of AZD9291 Aniline as synthesized according to example 2

| | HPLC analysis-area % [1] | | |
|---|---|---|---|
| Experiment | AZD9291 Aniline | AZD9291 Nitrodiamine | AZD9291 Aniline Hydroxy |
| A | 98.67 | ND | ND |
| B | 98.47 | ND | ND |
| C | 98.54 | ND | 0.16 |
| D[2] | No data | No data | No data |
| E | 97.37 | ND | 0.76 |
| F | 98.99 | ND | ND |
| G | 99.17 | ND | ND |
| H | 99.23 | ND | ND |
| J[3] | 96.36 | ND | ND |
| K | 98.73 | 0.43 | ND |
| L | 78.10 | 20.59 | ND |
| M | 98.89 | ND | ND |
| N | 99.00 | ND | ND |
| P | 98.94 | ND | ND |
| Q | 99.14 | ND | ND |
| R | 99.21 | ND | ND |
| S | 98.91 | ND | ND |
| T | 98.98 | ND | ND |
| U | 98.67 | ND | ND |
| V | 98.93 | ND | ND |
| W | 96.68 | ND | 0.10 |
| X | 94.00 | 4.93 | ND |

[1] ND = non-detected. Estimated detection limit of method is <0.1 area %
[2] No reaction or a very slow reaction was observed for this experiment. No HPLC data collected.
[3] Non-detectable levels of AZD9291 Aniline Hydroxy were observed in this experiment, however, other impurities, due to presence of acetone in the reaction mixture, were observed. The level of total other impurities was determined as 2.91 area %.

The invention claimed is:

1. A process for the preparation of AZD9291 or a pharmaceutically acceptable salt thereof, which comprises:
  a) reaction of AZD9291 Nitrodiamine of formula (III) or a salt thereof

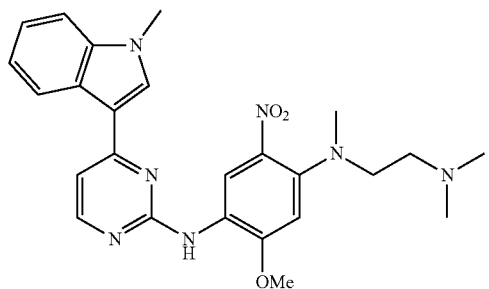

(III)

with hydrogen, in the presence of a palladium(0)- and/or platinum(0)-based catalyst, and in the presence of an acid, to form AZD9291 Aniline of formula (I) or a salt thereof

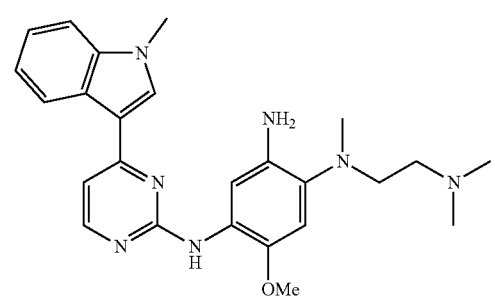

(I)

wherein the reaction is carried out in the presence of water, or in the presence of a mixture of water and a water-miscible solvent;
  b) reaction of the resulting AZD9291 Aniline or a salt thereof with an activated acrylic acid derivative or precursor, and where necessary, treatment with base to form AZD9291 of formula (II):

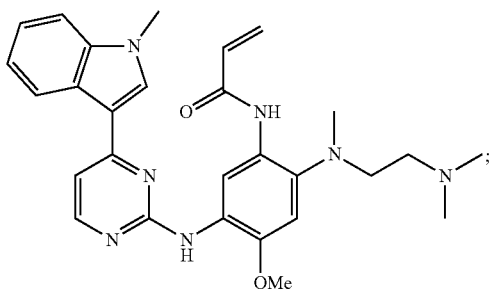

and c) optional formation of a pharmaceutically acceptable salt thereof.

2. A process for the preparation of AZD9291 Aniline or a salt thereof which comprises step a) of the process as claimed in claim 1.

3. A process as claimed in claim 1 or claim 2, wherein the acid comprises an acid selected from a carboxylic acid, a sulfonic acid and a mineral acid.

4. A process as claimed in claim 3 wherein the carboxylic acid comprises an acid selected from ($C_{1-7}$hydrocarbyl)COOH, formic acid, trichloroacetic acid and trifluoroacetic acid.

5. A process as claimed in claim 3 wherein the sulfonic acid comprises an acid selected from methanesulfonic acid, benzenesulfonic acid and p-toluenesulfonic acid.

6. A process as claimed in claim 3 wherein the mineral acid comprises an acid selected from hydrochloric acid, sulfuric acid and phosphoric acid.

7. A process as claimed in claim 1 or claim 2 wherein at least 1.0 molar equivalents of acid is used.

8. A process as claimed in claim 1 or claim 2 wherein 1.0-2.0 molar equivalents of acid is used.

9. A process as claimed in claim 1 or claim 2 wherein 1.5 molar equivalents of acid is used.

10. A process as claimed in claim 1 or claim 2 wherein the palladium(0)- and/or platinum(0)-based catalyst comprises a palladium(0)-based catalyst.

11. A process as claimed in claim 1 or claim 2 wherein the palladium(0)- and/or platinum(0)-based catalyst contains at least 0.0005 molar equivalents of palladium(0).

12. A process as claimed in claim 1 or claim 2 wherein the palladium(0)- and/or platinum(0)-based catalyst comprises a platinum(0)-based catalyst.

13. A process as claimed in claim 1 or claim 2 wherein the palladium(0)- and/or platinum(0)-based catalyst contains at least 0.0001 molar equivalents of platinum(0).

14. A process as claimed in claim 1 or claim 2 wherein the water-miscible solvent is selected from an alcohol, tetrahydrofuran, acetonitrile, dimethyl sulfoxide, dimethylformamide, dimethylacetamide and N-methylpyrrolidin-2-one.

15. A process as claimed in claim 1 or claim 2 wherein the water-miscible solvent is selected from methanol, iso-propanol, tetrahydrofuran, acetonitrile, dimethyl sulfoxide and N-methylpyrrolidin-2-one.

16. A process as claimed in claim 1 or claim 2 wherein the reaction of AZD9291 Nitrodiamine of formula (III), or a salt thereof, is carried out in the presence of water.

17. A process as claimed in claim 1 wherein the activated acrylic acid derivative or precursor is acryloyl chloride or 3-chloropropanoyl chloride.

18. A process as claimed in claim 1 wherein the activated acrylic acid derivative or precursor is acryloyl chloride.

19. A process as claimed in claim 1 wherein the activated acrylic acid derivative or precursor is 3-chloropropanoyl chloride.

* * * * *